(12) United States Patent
Da Silva Arnaut Moreira et al.

(10) Patent No.: US 9,670,217 B2
(45) Date of Patent: Jun. 6, 2017

(54) PROCESS FOR PREPARING CHLORINS AND THEIR PHARMACEUTICAL USES

(75) Inventors: Luis Guilherme Da Silva Arnaut Moreira, Coimbra (PT); Maria Miguéns Pereira, Coimbra (PT); Sebastião José Formosinho SanchesSimões, Coimbra (PT); Sérgio Paulo Magalhães Simões, Coimbra (PT); Grazyna Stochel, Kraków (PL); Krystyna Urbanska, Iwanowicc (PL)

(73) Assignee: UNIVERSIDADE DE COIMBRA, Coimbra (PT)

( * ) Notice: Subject to any disclaimer, the term of this patent is extended or adjusted under 35 U.S.C. 154(b) by 1595 days.

(21) Appl. No.: 13/125,805

(22) PCT Filed: Oct. 22, 2009

(86) PCT No.: PCT/PT2009/000057
§ 371 (c)(1),
(2), (4) Date: Jun. 29, 2011

(87) PCT Pub. No.: WO2010/047611
PCT Pub. Date: Apr. 29, 2010

(65) Prior Publication Data
US 2011/0250143 A1     Oct. 13, 2011

(30) Foreign Application Priority Data
Oct. 24, 2008 (GB) .................................. 0819594.3

(51) Int. Cl.
C07D 487/22 (2006.01)
(52) U.S. Cl.
CPC .................................. C07D 487/22 (2013.01)
(58) Field of Classification Search
CPC ..... C07D 487/22; A61K 49/06; A61K 31/407
USPC ................................ 424/9.61, 9.362; 540/145
See application file for complete search history.

(56) References Cited

U.S. PATENT DOCUMENTS

| | | | |
|---|---|---|---|
| 3,989,816 | A | 11/1976 | Rajadhyaksha |
| 4,326,893 | A | 4/1982 | Clifford |
| 4,405,616 | A | 9/1983 | Rajadhyaksha |
| 4,562,075 | A | 12/1985 | Rajadhyaksha |
| 5,831,088 | A | 11/1998 | Dolphin et al. |
| 5,864,035 | A | 1/1999 | Pandey et al. |
| 6,376,483 | B1 | 4/2002 | Robinson |
| 6,569,846 | B1 | 5/2003 | Scherz et al. |
| 6,624,187 | B1 | 9/2003 | Pandey et al. |
| 7,166,719 | B2 | 1/2007 | Pandey et al. |
| 2006/0194960 | A1 | 8/2006 | Kim et al. |
| 2009/0149525 | A1 | 6/2009 | Miguens Pereira et al. |

FOREIGN PATENT DOCUMENTS

| | | |
|---|---|---|
| EP | 2 123 664 A1 | 11/2009 |
| WO | 90/12573 A1 | 11/1990 |
| WO | 91/01727 A2 | 2/1991 |
| WO | 94/00118 A1 | 1/1994 |
| WO | 95/32206 A1 | 11/1995 |
| WO | 96/13504 A1 | 5/1996 |
| WO | 97/32885 A1 | 9/1997 |
| WO | 03/020309 A2 | 3/2003 |
| WO | 03/064427 A1 | 8/2003 |
| WO | 2006/053707 A1 | 5/2006 |
| WO | 2008/102669 A1 | 8/2008 |

OTHER PUBLICATIONS

Tanaka et al., Chem. Rev., 2000, 100, p. 1025-1074.*
Database; Chemical Abstracts Service, Columbus, Ohio, US; Jan. 4, 1993; Sutter, Timothy P.G. et al.; "Steric and inductive effects on the basicity of porphyrins and on the site of protonation of porphyrin dianions: radiolytic reduction of porphyrins and metalloporphyrins to chlorins or phlorins"; XP002565503.
Database; Chemical Abstracts Service, Columbus, Ohio, US; Jan. 5, 2009; Pereira, Mariette M. et al.; Synthesis and photophysical properties of amphiphilic halogenated bacteriochlorins: new opportunities for photodynamic therapy of cancer:; XP002574198.
Singh J. et al.; "Transdermal Lontophoresis: Effect of Penetration Enhancer and Lontophoresis on Drug Transport and Surface Characteristics of Human Epidermis"; Current Problem in Dermatology, Karger, Basel, CH; vol. 22, Jan. 1, 1995, pp. 179-189; XP008019183.
International Search Report for PCT/PT2009/000057 dated Apr. 1, 2010.
Pereira, M.M. et al. (2012) An insight into solvent-free diimide porphyrin reduction: a versatile approach for meso-aryl hydroporphyrin synthesis. *Green Chem.* 14, 1666.

* cited by examiner

*Primary Examiner* — Michael G Hartley
*Assistant Examiner* — Leah Schlientz
(74) *Attorney, Agent, or Firm* — John P. White; Cooper & Dunham LLP

(57) ABSTRACT

The disclosed subject matter includes methods of preparation, properties, pharmaceutical compositions and methods of therapy of sulfonated chlorins and bacteriochlorins designed for the photodynamic therapy (PDT) of hyperproliferative tissues such as tumors, hyperproliferative blood vessels and other disorders or abnormalies that are responsive to PDT. In particular, the economical large-scale synthesis of stable chlorins and bacteriochlorins is described. Their properties were tailored to meet those of ideal photosensitizers for PDT. In another embodiment, pharmaceutical compositions and methods of therapy for systemic administration are provided. In a further embodiment, pharmaceutical compositions and methods of therapy for topical administration are also provided. Further provided is a method of labeling a target tissue and providing an image of that tissue by fluorescence of magnetic resonance imaging.

4 Claims, 14 Drawing Sheets

PROCESS FOR PREPARING CHLORINS AND THEIR PHARMACEUTICAL USES

Figure 1:
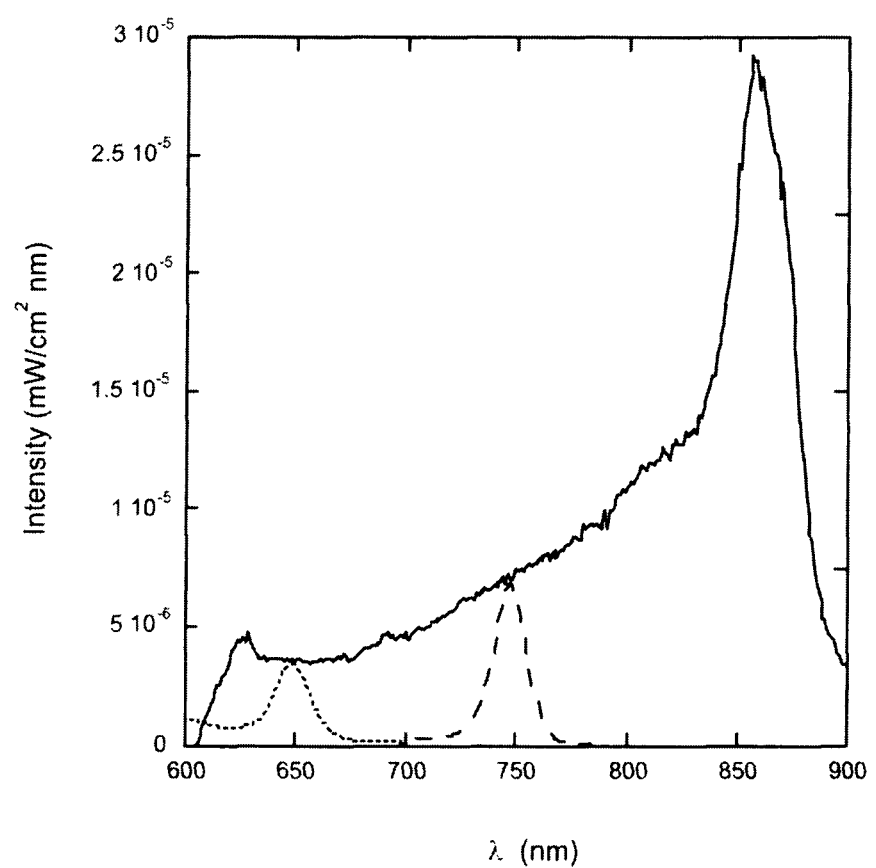

This application is a U.S. national phase filing under 35 U.S.C. §371 of PCT Application No. PCT/PT2009/000057, filed Oct. 22, 2009, the entirety of which is hereby incorporated by reference herein.

FIELD OF THE INVENTION

The present invention relates to the methods of preparation, properties, pharmaceutical compositions and use in therapy of sulfonated chlorins and bacteriochlorins designed for the photodynamic therapy (PDT) of hyperproliferative tissues such as tumors, hyperproliferative blood vessels and other disorders or anomalies that are responsive to PDT. In particular, the present invention relates to a novel method capable of chemically synthesizing stable chlorins and bacteriochlorins in a large scale, which is characterized by the absence of solvent and the absence of base. In another embodiment, pharmaceutical compositions and methods for their use in therapy with systemic administration are provided. In a further embodiment, pharmaceutical compositions and methods for their use in therapy with topical administration are also provided. Also provided are methods for the detection of hyperproliferative tissues such as tumors, using photodynamic methods or MRI.

I. BACKGROUND OF THE INVENTION

I.A. State-of-the-Art

Various tetrapyrrolic macrocycles, such as purpurins, chlorins, bacteriochlorins, phthalocyanines and benzochlorins, have shown the ability both to preferentially collect in hyperproliferative tissues when injected into an organism, and to absorb light to form an activated state in response to the light. These macrocycles then exhibit a cytotoxic effect on the cells or other tissues in which they are localized when irradiated at the appropriate wavelength. Moreover, these compounds also cause emission of energy from the tissue that can be used to detect their location.

In PDT the patient is injected with a photosensitizer (usually between about 0.1 and about 10 mg/kg of body weight) which shows some selectivity for photodamage to tumor tissue and then, after a certain time, the tumor area is irradiated with visible or near-infrared light (from about 50 to 200 J/cm$^2$). The photosensitizer absorbs light and fluoresces, or reacts with substrate molecules in the tissues by electron or hydrogen transfer reactions (Type I processes), or transfers its energy to ground-state molecular oxygen generating singlet oxygen $O_2$ ($^1\Delta_g$) that attacks the tissues (Type II process). A major contributor to Type I process is the superoxide ($O_2^-$), formed by electron transfer from the electronically excited sensitizer. There is evidence favoring the Type II photooxygenation process over Type I processes in cells [1,2], but there are also claims of an amplified PDT response when superoxide is also generated [3]. In the case of detection, fluorescence is determined upon exposure to light at the desired wavelength, and lower energies are required than for treatment. Efficient treatment usually requires the formation of high yields of singlet oxygen in the tissue, which may have a synergistic effect with the concomitant formation of superoxide or other reactive oxygen species.

The properties of optimal sensitizers for PDT treatment include: (i) simple, efficient and economical synthesis; (ii) stability, purity and long shelf-life; (iii) solubility in biocompatible solvents or vehicles; (iv) high absorption coefficient in the "phototherapeutic window" (600-900 nm); (v) singlet molecular oxygen sensitization and/or superoxide generation with a high quantum yield; (vi) reduced or no dark toxicity; (vii) selective accumulation and prolonged retention in tumor tissues; (viii) low skin photosensitization under systemic administration; (ix) controlled photobleaching; (x) facile metabolism or excretion after treatment. The sensitizer is only the precursor of the cytotoxic species, notably singlet oxygen and other reactive oxygen species such as the superoxide ion. The immediate precursor of singlet oxygen, and often of superoxide, is the triplet state of the sensitizer. Thus, a high singlet oxygen quantum yield requires at least three sensitizer triplet state properties: (i) a near unity quantum yield, (ii) an electronic energy at least 20 kJ/mol above that of singlet oxygen (94 kJ/mol), (iii) and a long lifetime (hundreds of microseconds). The accumulation and retention in tumor tissues can be enhanced with the addition of specific vectors, but a relevant intrinsic property of the sensitizer for these purposes is the hydrophilicity/lipofilicity of the sensitizer and the ability to tailor such properties to attain desired targets is a most welcome property.

The lower end of the phototherapeutic window is determined by the presence of heme proteins, that account for most of the absorption of light in the visible region in tissues. The penetration of light in tissues drops off rapidly below 550 nm. However, there is a significant increase in penetration from 550 to 630 nm, and penetration doubles again to 700 nm. This is followed by a 10% increase in tissue penetration as the wavelength moves towards 800 nm. The higher end of the phototherapeutic window is determined by the absorption of infrared radiation by water and by the energy requirements for efficient energy transfer to oxygen. Indeed, diffusion-controlled triplet energy transfer from the sensitizer to molecular oxygen requires that the triplet energy of the sensitizer is at least 115 kJ/mol. Additionally, the singlet-triplet energy splitting in tetrapyrrolic macrocycles is ca. 40 kJ/mol [4], which requires that the sensitizer must have a singlet energy larger than 150 kJ/mol. Considering that the Stokes shift of such these sensitizers is usually small, they should absorb light just below 800 nm. The conclusion is that an ideal sensitizer must strongly absorb light with wavelengths ca. 750 nm. The strong absorption of bacteriochlorins at this wavelength makes them ideal candidates for PDT sensitizers. For applications where light penetration is not as critical, chlorins are also suitable candidates for PDT.

Photofrin®, a hematoporphyrin derivative [5], is the most widely used photosensitizer, and has been approved for the treatment of a variety of solid tumors [6]. Hematoporphyrin derivative (HpD) is prepared by mixing hematoporphyrin with glacial acetic acid and sulfuric acid, followed by hydrolysis and precipitation under acidic conditions. This method was partially described by Lipson et al [7]. HpD thus produced consists of a complex mixture of porphyrins. When HpD is separated into its two main fractions by gel filtration with Sephadex LH-20, the higher molecular weight portion, called Photofrin®, is a more efficient PDT agent [8]. The recommended human dosage of Photofrin® is 1-2 mg/kg of body weight. The main components of Photofrin® are dimers and higher oligomers linked with ether, ester and possibly carbon-carbon linkages [9].

Photofrin® has some desirable characteristics, including good efficacy, water solubility, reasonable yield of singlet oxygen, and ease of manufacture. However, Photofrin® also has some disadvantageous properties: (i) it is a complex mixture of porphyrin dimers and higher oligomers linked by ether, ester, and/or carbon-carbon bonds; (ii) it shows skin phototoxicity in patients for four to six weeks after administration; (iii) due to its relatively weak absorbance in the red region (630 nm), lack of penetration of light through tissue limits current clinical applications of Photofrin® in PDT to the destruction of cancerous tissue located less than 4 mm from the source of light used in the therapy. Thus, there is a need for more efficient, chemically pure, less phototoxic, better localizing sensitizers that absorb light more intensely and in the infrared.

It is known in the art that the chemical reduction of one of the tetrapyrrole rings, corresponding to the transformation of a porphyrin into a chlorin, leads to a displacement of the longest wavelength absorption band further into the red, concomitant with an increase of its absorption coefficient. Such properties were explored in the second-generation of PDT photosensitisers, and 5,10,15,20-tetrakis(3-hydroxyphenyl)chlorin (m-THPC), commercialized under the name Foscan®, emerged as one of the most potent of this second-generation photosensitisers [10]. Further reduction of the opposite pyrrole ring, corresponding to the transformation of a chlorin into a bacteriochlorin, leads to the displacement of the absorption band into the infrared and an additional increase of its absorption coefficient. However, until recently, it was a widely shared belief that bacteriochlorins are very unstable compounds [10] and research efforts on PDT sensitizers focused on chlorins [11]. Subsequently, it has been shown that stable bacteriochlorins can indeed be synthesized [12]. This was not fully appreciated in the scientific literature, where it was claimed that synthesis of stable bacteriochlorins with this approach was limited for preparing bacteriochlorins with inert functionalities [13]. However, bacteriochlorins with further functionalities have been prepared (see PCT/EP2005/012212, WO/2006/053707).

The obvious interest of bacteriochlorins as PDT sensitizers and reports that some naturally occurring bacteriochlorins were effective photosensitizers both in vitro and as in vivo [14,15], motivated many attempts to synthesize bacteriochlorins. Synthetic bacteriochlorins have been prepared by derivatization of the corresponding porphyrins via vicinal dihydroxylation with osmium tetroxide [16], intramolecular cyclization [17], Diels-Alder reactions using porphyrins as dienophile [18] or Diels-Alder reactions with vinyl porphyrins where the porphyrin is the diene [19], via 1,3-dipolar cycloaditions [20] and also by self-condensation of dehydrodipyrrin-acetal derivatives [21]. Additionally, there is the classic method, developed several decades ago by Whitlock for preparing bacteriochlorins, by reduction the 7,8-17,18-pyrrolic porphyrin positions with diimide [22]. This was the method used by Bonnet to synthesize Foscan and 5,10,15,20-tetrakis(3-hydrophenyl)bacteriochlorin [23]. Meanwhile, the very intensive research carried out on the synthesis of bacteriochlorin derivatives lead to a number of patents based on the methods described above (see, for example, US2007/7,166,719; US2003/6,624,187; US2003/6,569,846; US2002/6,376,483; US1999/5,864,035; US1998/5,831,088; WO90/12573; WO94/00118; WO95/32206; WO96/13504; WO97/32885; US2006/194,960).

Some of the newly synthesized bacteriochlorins have a negligible dark toxicity and a high tumor selectivity, are partially water soluble and have marked absorption bands in the range from 700 nm to 800 nm. However, some disadvantages remain, namely: (i) a complicated and expensive synthesis involving laborious purifications; (ii) limited water solubility which, in the case of a systemic application, results in a dissolution in organic solvents, with an additional chemical burden on the organism, or binding to a vehicle, increasing the cost of the treatment; (iii) chemical instability, specially in the presence of light; (iv) low or unknown singlet oxygen quantum yields. An interesting representative of this third generation of photosensitizers is a palladium-bacteriopheophorbide currently known as Tookad®, which has been approved for Phase III clinical studies. Tookad® is derived from bacteriochlorophyll and, as most of the naturally occurring bacteriochlorins, is very sensitive to oxygen, which results in rapid oxidation to the chlorin state, which has an absorption maximum at or below 660 nm. Furthermore, if a laser is used to excite the bacteriochlorin in vivo, oxidation may result in the formation of a new chromophore absorbing outside the laser window, which reduces the photosensitizing efficacy. The photochemical degradation of this family of compounds was measured with 778 nm (13 mW) illumination in TX-100/PBS, and revealed that 90% of the compound was irreversibly lost in 5 min (4 J), with the concomitant growth of a chlorin band at 660 nm [3].

PDT has also been extensively tested for the treatment of skin disorders, namely actinic keratoses, squamous cell carcinoma, Bowen's disease (intra-epithelial squamous cell carcinoma), basal cell carcinoma, but little information is available on malignant melanoma [24]. The high pigmentation of melanoma tissues limits the efficiency of PDT when visible light is employed, because melanin attenuates light penetration in tissues for wavelengths below 700 nm. There are also reports of topical PDT use in nontumoral condition, such as psoriasis. Earlier studies employed hematoporphyrin derivative [25] and meso-tetraphenylporphinesulfonate tetrasodium salt [26] in liquid formulations containing percutaneous penetration enhancers. However, typically, when HpD or other porphyrins are applied topically in a (liquid, gel, cream, emulsion, etc.) formulation containing a vehicle intended to enhance their diffusion through tissue, the porphyrins tend to be retained as the dilution of the permeation enhancer by normal tissue fluids takes place. In such circumstances, the porphyrins can no longer diffuse through the tissue (or even remain in solution). Consequently, the topical application of porphyrins often is associated with a loss of specificity for malignant tissues, and normal tissues near the site of application may develop persistent photosensitization as a result of the localized concentration of porphyrin To overcome these problems, it was suggested that rather than applying a porphyrin topically it would be advantageous to use an agent which is not in itself a photosensitizer but which induces the synthesis of endogenous porphyrins in vivo, namely protoporphyrin-IX (PpIX) [27]. It is known that 5-amino-4-oxopentanoic acid, otherwise known as 5-aminolevulinic acid (or ALA), is a biological precursor or protoporphyrin IX. An excess of ALA leads to a biological accumulation of PpIX, which is the actual photosensitizing agent. Thus, by applying ALA topically to skin tumors, and then after several hours exposing the tumors to light, a beneficial phototherapeutic effect may be obtained (see, for example, WO91/01727). Since the skin covering basilomas and squamous cell carcinomas is more readily penetrated by ALA than healthy skin, and since the biosynthesis of PpIX is more efficient in skin tumors, it has been found that topical application of ALA leads to a selectively enhanced production of PpIX in tumors. This has been the basis for a number of dermatological formulations of ALA, or some of its derivatives, that have been approved and are in clinical use, most notably Levulan® and Metvix®.

However, whilst the use of ALA represents a significant advance in the art, photodynamic therapy with ALA is not entirely satisfactory. Patients repeatedly report having experienced pain in ALA-PDT [28]. ALA is a pro-dug and the efficiency of the drug production varies with the biosynthesis in the subject. Only a very limited amount of PpIX can be biosynthesized by the cells. It tends to be unstable in pharmaceutical formulations. It is not able to penetrate all tumors and other tissues with sufficient efficacy to enable treatment of a wide range of tumors or other conditions. Its preferred wavelength of the photoactivating light is about 635 nm, whereas it has been shown that only between 1 and 10 percent of incident red light (600-700 nm) can pass through a slab of human tissue 1 cm thick. A need therefore exists for improved photodynamic therapeutic agents for topical applications.

I.B. Summary of the Invention

According to a first aspect, the present invention provides a process for the preparation of a chlorin or bacteriochlorin derivative having the formula:

Formula (I)

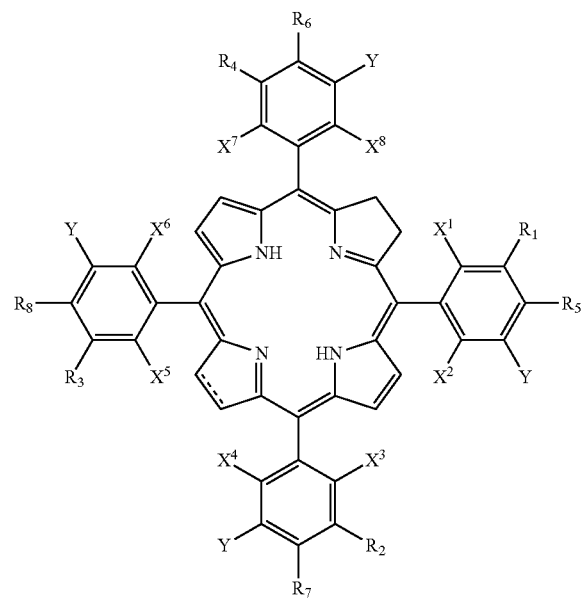

wherein:
::::: represents a carbon-carbon single bond or a carbon-carbon double bond;
$X^1$, $X^2$, $X^3$, $X^4$, $X^5$, $X^6$, $X^7$, $X^8$ are each independently chosen from halogen (F, Cl, Br) and hydrogen atoms, provided that either all of $X^2$, $X^4$, $X^6$ and $X^8$ or all of $X^1$, $X^3$, $X^5$ and $X^7$ are halogens, or all X are halogens;
$R_1$, $R_2$, $R_3$, $R_4$, $R_5$, $R_6$, $R_7$, $R_8$, are independently chosen from H, —OH and —$SO_2R$, where R are each independently chosen from —Cl, —OH, -aminoacid, —OR″, —NHR″ and —$NR_2″$ where R″ are alkyl of 1 to 12 carbon atoms;
$R_1$, $R_2$, $R_3$, $R_4$, $R_5$, $R_6$, $R_7$, $R_8$, are independently chosen from H, —OH and —$SO_2R$, where R are each independently chosen from —Cl, —OH, -aminoacid, —OR″, —NHR″ and —$NR_2″$ where R″ are alkyl of 1 to 12 carbon atoms;
Y is either fluorine or hydrogen;
comprising the following step:
(i) the solid-state reduction of the corresponding substituted porphyrin to the chlorin derivative or bacteriochlorin derivative using hydrazides in the absence of solvents and, optionally, in the absence of bases; wherein the corresponding substituted porphyrin has the formula:

Formula (II)

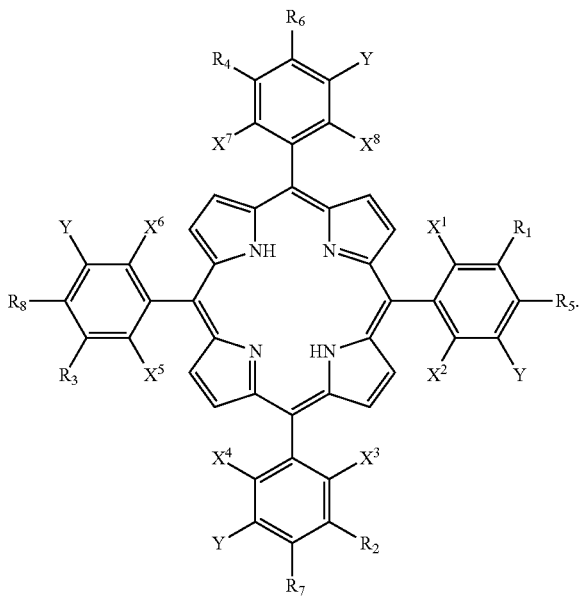

Hence, the compound of Formula (I) may be a chlorin derivative having the formula:

Formula (V)

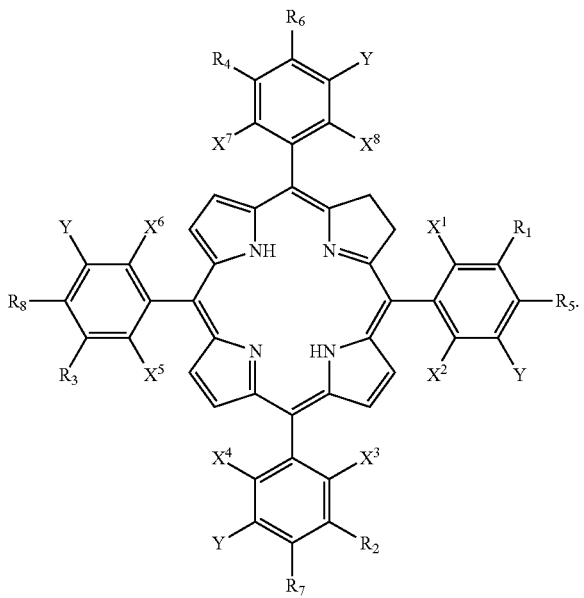

Alternatively, the compound of Formula (I) may be a bacteriochlorin derivative having the formula Formula (VI)

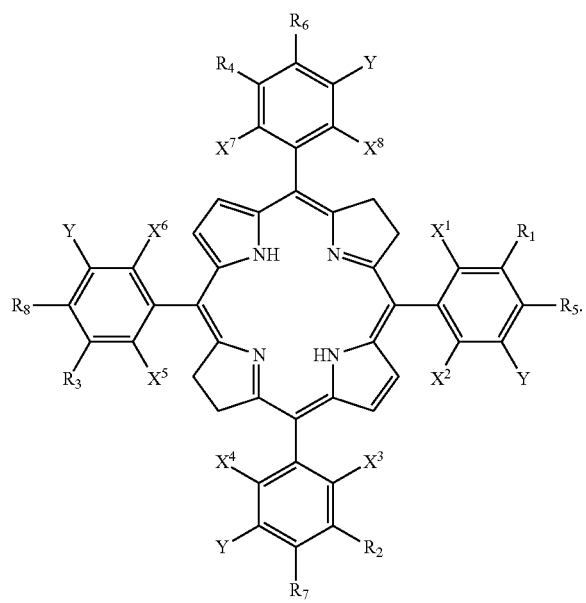

Suitably $X^2$, $X^4$, $X^6$, $X^8$ are each independently chosen from halogen (F, Cl, Br).

Suitably $R_5$, $R_6$, $R_7$, $R_8$, are H.

Suitably Y is H.

Suitably $R_1$, $R_2$, $R_3$, $R_4$, are —$SO_2R$, where R are each independently chosen from —Cl, —OH, -aminoacid, —OR″, —NHR″ and —$NR_2″$ where R″ are alkyl of 1 to 12 carbon atoms.

In a further aspect, $X^2$, $X^4$, $X^6$, $X^8$ are each independently chosen from halogen (F, Cl, Br);

$R_5$, $R_6$, $R_7$, $R_8$, are H;

Y is H; and $R_1$, $R_2$, $R_3$, $R_4$, are —$SO_2R$, where R are each independently chosen from —Cl, —OH, -aminoacid, —OR″, —NHR″ and —$NR_2″$ where R″ are alkyl of 1 to 12 carbon atoms.

In a further aspect, the present invention provides a process for the preparation of a chlorin or bacteriochlorin derivative having the formula:

Formula (III)

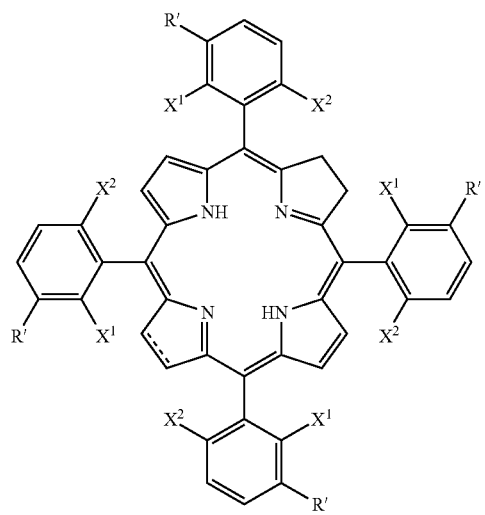

wherein:

⁝⁝⁝ represents a carbon-carbon single bond or a carbon-carbon double bond;

$X^2$ are chosen from halogen (F, Cl, Br), $X^1$ are chosen from hydrogen or halogen (F, Cl, Br); and R' are —$SO_2R$, where R are each independently chosen from —Cl, —OH, -aminoacid, —OR″, —NHR″ and —$NR_2″$ where R″ are alkyl of 1 to 12 carbon atoms, comprising the following step:

(i) the solid-state reduction of the corresponding substituted porphyrin to the chlorin derivative or bacteriochlorin derivative using hydrazides in the absence of solvents and, optionally, in the absence of bases; wherein the corresponding substituted porphyrin has the formula:

Formula (IV)

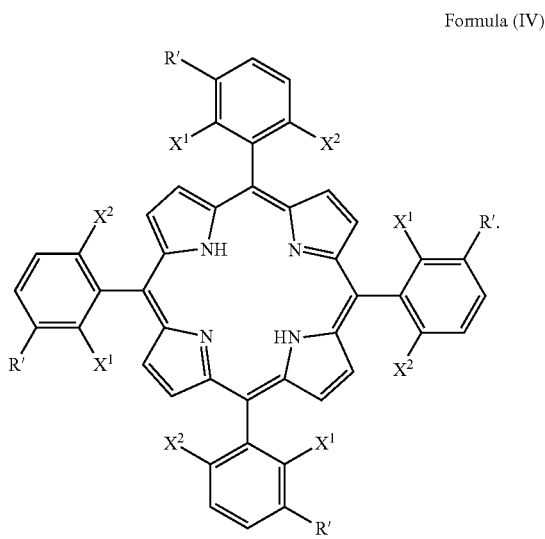

Hence, the compound of Formula (III) may be a chlorin derivative having the formula:

Formula (VII)

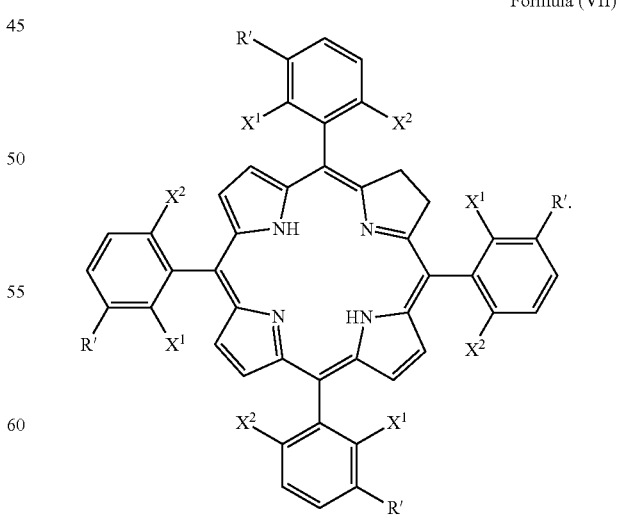

Alternatively, the compound of Formula (III) may be a bacteriochlorin derivative having the formula Formula (VIII)

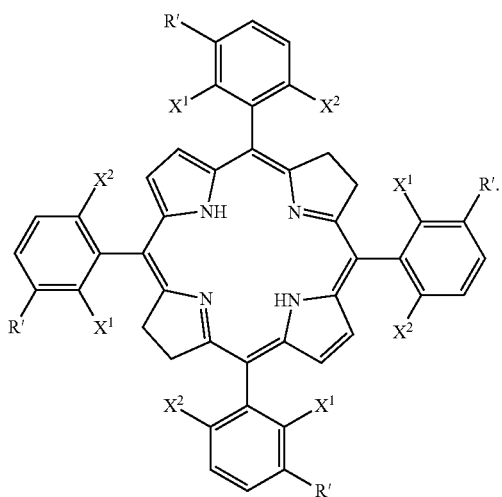

In a further aspect, R' is —SO$_2$R, where R is —Cl for the corresponding substituted porphyrin of Formula (IV); and the process comprises the further step of:

(ii) bonding the chlorin or a bacteriochlorin derivative with an amine H—NHR" or H—NR$_2$"; an aminoacid, or an alcohol H—OR", where R" are alkyl of 1 to 12 carbon atoms;

to provide a chlorine or bacteriochlorin derivative wherein, R' is —SO$_2$R, where R is -aminoacid, —OR", —NHR" or —NR$_2$" where R" are alkyl of 1 to 12 carbon atoms.

In a further aspect, the present invention provides a pharmaceutical composition comprising:

(a) a chlorin or a bacteriochlorin derivative having the formula:

Formula (III)

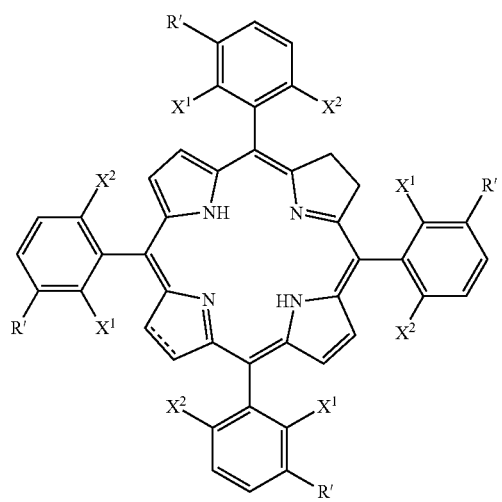

or a pharmaceutically acceptable composition derivative thereof, wherein:

⁓ represents a carbon-carbon single bond or a carbon-carbon double bond;

X$^2$ are chosen from halogen (F, Cl, Br), X$^1$ are chosen from hydrogen or halogen (F, Cl, Br), and R' are —SO$_2$R;

R are each independently chosen from —Cl, —OH, -aminoacid, —OR", —NHR" and —NR$_2$" where R" are alkyl of 1 to 12 carbon atoms, wherein the chlorin or bacteriochlorin derivative is effective in a photodynamic therapy treatment for ameliorating the symptoms of a hyperproliferative disorder; and (b) a surface penetration enhancer.

In a further aspect the present invention provides the use of a chlorin or a bacteriochlorin derivative, or a pharmaceutically acceptable composition derivative thereof, in the detection of hyperproliferative tissue;

wherein the chlorin or bacteriochlorin derivative has the formula:

Formula (III)

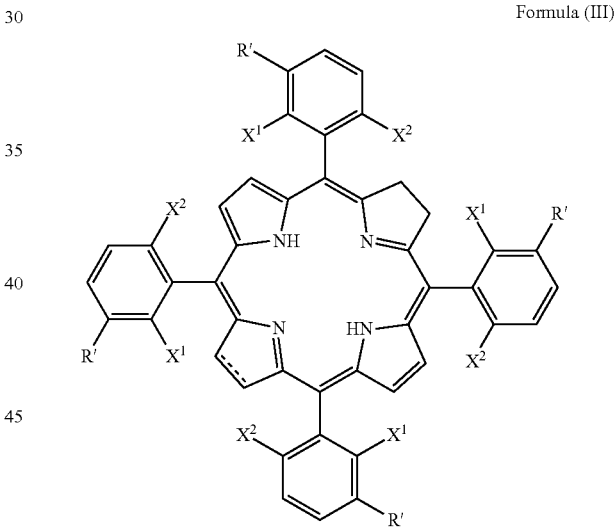

wherein:

⁓ represents a carbon-carbon single bond or a carbon-carbon double bond;

X$^2$ are chosen from halogen (F, Cl, Br), X$^1$ are chosen from hydrogen or halogen (F, Cl, Br), and R' are —SO$_2$R;

R are each independently chosen from —Cl, —OH, -aminoacid, —OR", —NHR" and —NR$_2$" where R" are alkyl of 1 to 12 carbon atoms, In a further aspect of the present invention there is provided a method for detecting the presence of a hyperproliferative tissue in a subject comprising:

(i) administering to the subject a diagnostically sufficient quantity of a chlorin or bacteriochlorin derivative having the formula

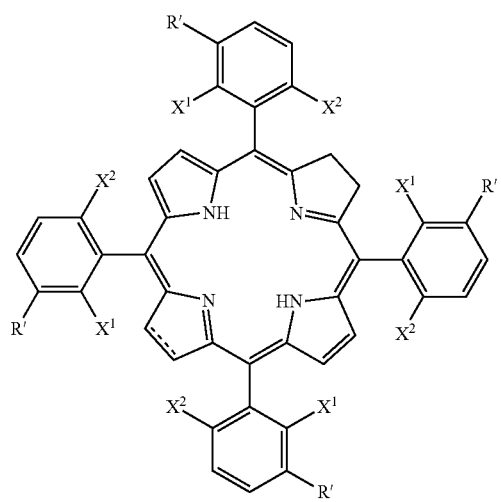

Formula (III)

wherein:

⁃⁃⁃⁃ represents a carbon-carbon single bond or a carbon-carbon double bond;

$X^2$ are chosen from halogen (F, Cl, Br), $X^1$ are chosen from hydrogen or halogen (F, Cl, Br), and R' are —SO$_2$R;

R are each independently chosen from —Cl, —OH, -amino-acid, —OR", —NHR" and —NR$_2$" where R" are alkyl of 1 to 12 carbon atoms, or a pharmaceutically acceptable composition derivative thereof that preferentially associates with the target, (ii) allowing sufficient time for the chlorin or bacteriochlorin derivative to associate with the target and for any chlorin or bacteriochlorin derivative that is not preferentially associated with the target tissue to clear from the non-target tissue, and (iii) visualizing the compound within the patient.

The step of visualizing may be accomplished by generating an MRI image of at least a part of the patient's body.

Alternatively, the step of visualizing may be accomplished by exposing the compound to light of sufficient energy to cause the compound to fluoresce.

In a further aspect of the present invention there is provided a pharmaceutically acceptable composition for use in the treatment of a skin cancer or of a skin disorder selected from actinic keratoses, squamous cell carcinoma, Bowen's disease, basal cell carcinoma, psoriasis, acne vulgaris and rosacea;

wherein the composition comprises:

(i) a chlorin or bacteriochlorin derivative with the formula:

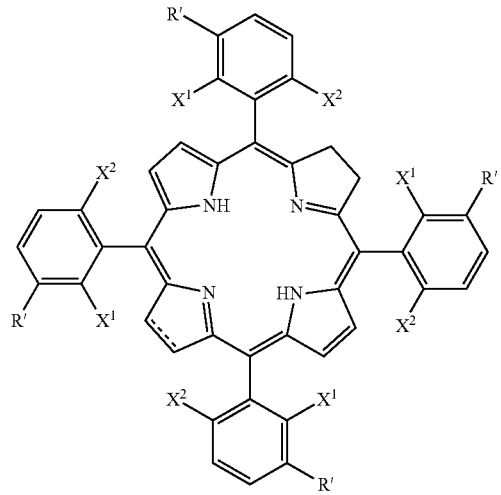

Formula (III)

wherein:

⁃⁃⁃⁃ represents a carbon-carbon single bond or a carbon-carbon double bond;

$X^2$ are chosen from halogen (F, Cl, Br), $X^1$ are chosen from hydrogen or halogen (F, Cl, Br), and R' are —SO$_2$R;

R are each independently chosen from —Cl, —OH, -amino-acid, —OR", —NHR" and —NR$_2$" where R" are alkyl of 1 to 12 carbon atoms;

and (ii) a pharmaceutically acceptable carrier for intradermal or transdermal delivery of such compound, wherein the carrier comprises a surface penetration enhancer that transiently permeabilizes the skin and facilitates the permeation of the compound through the various skin layers;

wherein (a) the composition is administered to a subject;

(b) sufficient time is allowed for the chlorin or bacteriochlorin derivative to preferentially locate near the target of the dermatological treatment; and (c) the target is irradiated to obtain the desired response of the skin cancer or of the skin disorder.

Process for the Preparation of the Derivatives

Suitably the hydrazine is p-toluenesulphonyl hydrazide, 4-chlorobenzenesulfonic hydrazide, 4,4'-oxybis(benzenesulfonyl)hydrazide, benzenesulfonyl hydrazide, 4-methoxybenzenesulfonyl hydrazide or benzoic hydrazide.

Solid-state reactions require the use of a temperature that is above the melting point of one of the reactants, such that the other reactant or reactants are partially dissolved, or dispersed, in the melted one. For the solid-state reactions between hydrazides and porphyrin derivatives the solid-state reaction is suitably carried out above the melting point of the hydrazide.

Suitably the reduction step is carried out at a temperature of at least 70° C. Suitably the reduction step is carried out at a temperature of at least 100° C. In a further aspect, reduction step is carried out at a temperature of from 70 to 200° C. Suitably, the reduction step is carried out for at least 5 minutes.

Suitably the reduction step is carried out under a vacuum or an inert atmosphere.

Pharmaceutical Compositions

Suitably the pharmaceutical composition comprises at least 0.01% by weight of the chlorin or bacteriochlorin derivative or a pharmaceutically acceptable salt thereof based on the overall weight of the composition. Suitably the pharmaceutical composition comprises from 0.01% to 30% by weight of the chlorin or bacteriochlorin derivative or a pharmaceutically acceptable salt thereof based on the overall weight of the composition. Suitably pharmaceutical composition comprises from 0.01% to 10% by weight of the chlorin or bacteriochlorin derivative or a pharmaceutically acceptable salt thereof based on the overall weight of the composition. Suitably pharmaceutical composition comprises from 0.1% to 1% by weight of the chlorin or bacteriochlorin or a pharmaceutically acceptable salt thereof derivative based on the overall weight of the composition.

When a surface penetration enhancer is present in a pharmaceutical composition, suitably the composition comprises 0.05 to 10% by weight of the surface penetration enhancer based on the overall weight of the composition. Suitably the composition comprises 0.1 to 10% by weight of the surface penetration enhancer. Suitably such surface penetration enhancer may be selected from dimethylsulphoxide and other dialkylsulphoxides, N-Methylformamide, dimethylformamide, dimethylacetamide, glycols, various pyrrolidone derivatives and various 1-substituted azacycloalkan-2-ones.

Suitable glycols may be selected from Polyethylene glycol, Polypropylene glycol 425, Trimethylene glycol and Propylene glycol monolaurate.

Suitable pyrrolidone derivatives may be selected from N-Dodecyl pyrrolidine-3,5-dione, N-Dodecyl pyrrolidine-2-thione, N-Dodecyl-2-pyrrolidone, N-(2, Hydroxyethyl)-2-pyrrolidone, N-Cyclohexyl-2-pyrrolidone, 1-Butyl-3-dodecyl-2-pyrrolidone, 1, 5 Dimethyl-2-pyrrolidone, 1-Ethyl-2-pyrrolidone, 1-Hexyl-4-methyloxycarbonyl-2-pyrrolidone, 1-Hexyl-2-pyrrolidone, 1-(2 Hydroxyethyl)pyrrolidinone, 3-Hydroxy-N-methyl-2-pyrrolidinone, 1-Lauryl-4-methyloxycarbonyl-2-pyrrolidone and N-Methyl-2-pyrrolidone.

Suitable 1-substituted azacycloalkan-2-ones including 1-dodecylazacycloheptan-2-one referred to hereinafter as Azone® are disclosed in U.S. Pat. Nos. 4,562,075, 4,405,616, 4,326,893 and 3,989,816.

Detection of Hyperproliferative Tissue

When chlorin and bacteriochlorin derivatives or pharmaceutically acceptable salts thereof are used in the detection of hyperproliferative tissue, suitably the hyperproliferative tissue may be selected from a vascular endothelial tissue, a neovasculature tissue, a neovasculature tissue present in the eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in the vascular system, a diseased bone marrow, and diseased cells in which the disease is one of an autoimmune and an inflammatory disease.

Treatment of Hyperproliferative Disorders

In a further aspect, the present invention provides the use of a chlorin or bacteriochlorin derivative as described herein, or a pharmaceutically acceptable salt thereof, in the manufacture of a medicament for use in the treatment of hyperproliferative disorders.

When chlorin or bacteriochlorin derivative or a pharmaceutically acceptable salts thereof are used in the treatment of hyperproliferative disorders, suitably the hyperproliferative disorder is selected from cancers or carcinomas, myelomas, psoriasis, macular degeneration. Suitable examples are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, head and neck cancer, cancer of the tongue, cerebral tumor, skin cancer, malignant goiter, prostatic cancer, colorectal cancer, cancer of the parotid gland, Hodgkin's disease, multiple myeloma, renal cancer, leukemia, and malignant lymphocytoma.

Such treatments suitably include irradiating the chlorin or bacteriochlorin derivative or pharmaceutically acceptable composition derivative thereof with light of a wavelength matching the absorption bands of the chlorine or bacteriochlorin derivative. Suitably the light has a wavelength of from 600 to 800 nm. Suitably when chlorins are used the light has a wavelength of from 630 to 690 nm. Suitably when bacteriochlorins are used the light has a wavelength of from 720 to 780 nm.

Suitably the light dose is from 1 to 250 J/cm$^2$. In some aspects, suitably the light dose is less than 50 J/cm$^2$, less than 20 J/cm$^2$, less than 10 J/cm$^2$.

Suitably the dosage of the chlorin or bacteriochlorin derivatives or pharmaceutically acceptable salts thereof is from 0.01 mg to 200 mg per kilogram of body weight per day. Suitably a dosage of from 0.01 mg to 100 mg per kilogram of body weight per day.

Figure 2:
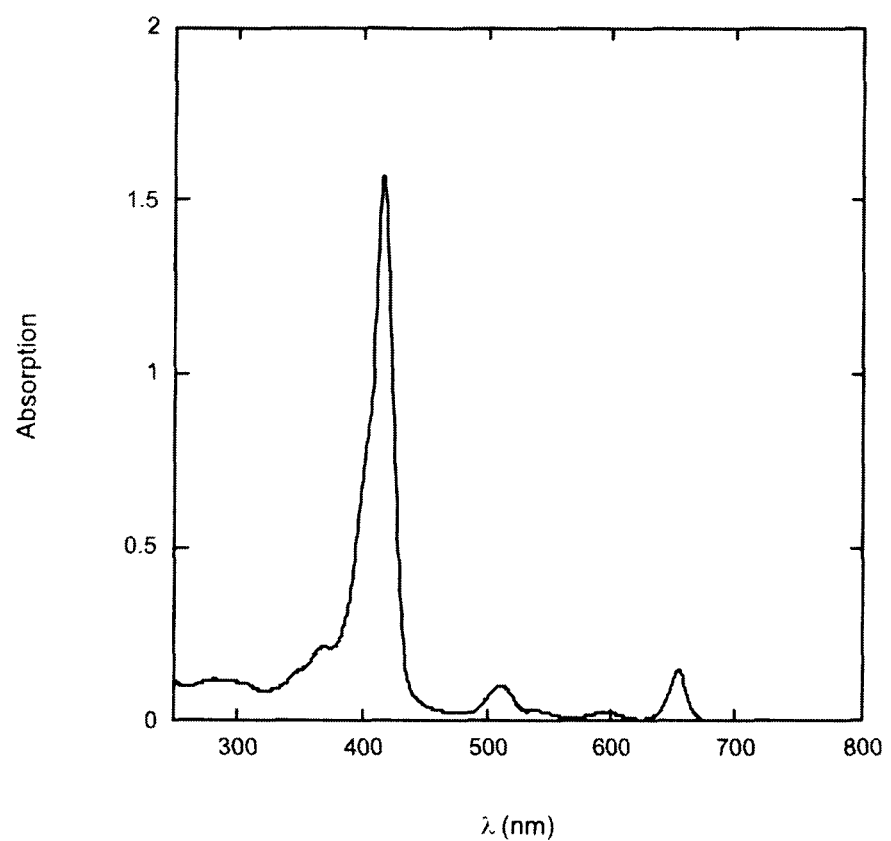

The present invention was made in view of the prior art described above. The synthesis described in WO 2006/053707 (PCT/EP2005/012212) comprised just three almost quantitative steps: (i) functionalization of halogenated tetrakisphenylporphyrins via chlorosulfonation of phenyl ring; (ii) synthesis of amphiphilic compounds via reaction of the chlorosulfonic group with nucleophiles, water, namely amines or alcohols; iii) reduction of the tetrapyrrolic macrocycle with hydrazide derivatives in the presence of inorganic or organic non-nucleophilic bases. However, as illustrated in FIG. 2 of patent WO 2006/053707, the synthesis of halogenated sulfonated bacteriochlorins by this method is associated with the contamination by the analogous chlorin, and the purification requires a laborious separation. The object of the present invention is to provide an economical, environmentally-friendly, large-scale synthesis of pure, stable and functionalized tetrakisphenylchlorins and tetrakisphenylbacteriochlorins bearing electron-withdrawing groups in the ortho positions of the phenyl rings. It is also an object of the present invention to provide chemical and therapeutic properties of said chlorins and bacteriochlorins, methods of therapy and pharmaceutical compositions with these molecules and evidence of their effectiveness in PDT.

Halogenated sulfonated bacteriochlorins have distinct features that make them preferred photosensitizers for PDT:

1) The presence of halogen atoms in the ortho positions of the phenyl groups performs three functions. First, they produce a controlled "heavy atom effect", increasing the yield of the sensitizer triplet state without compromising the triplet lifetime and its ability to transfer the electronic energy efficiently to molecular oxygen [29]. Second, they stabilize the reduced state of tetrapyrrolic macrocycles, both by electronic and steric effects. Third, they accelerate the rate constant of energy transfer to molecular oxygen through charge transfer interactions, leading to large yields of singlet oxygen, superoxide and other reactive oxygen species.

2) The presence of the sulfonic acid group in the meta positions of the phenyl groups performs two functions. First, it provides a handle to tailor the hydrophilicity/lipophilicity of the sensitizers, because very hydrophobic sensitizers seem to be less phototoxic, probably due to the low solubility and low ability to relocate from the plasma membrane into other intracellular compartments, whereas very hydrophilic dyes may predominantly localize in the tumor stroma and have reduced PDT efficacy [30]. Second, the sulfonic group, especially with bulky or long substituents attached to it, provides an additional steric protection against the oxidation of the bacteriochlorin core of the dyes.

3) The simultaneous presence of halogen atoms in the ortho positions and sulfonic acid group in the meta positions of the phenyl groups performs an additional function. Molecular modeling and experimental data show that when there is a restricted rotation of the single bond at the meso-position on 5,10,15,20-tetraphenylporphyrins with unsymmetrical phenyl rings, geometric isomers (known as atropisomers) result from the different position of the ortho and/or mew substituents relative to the porphyrin plane [31]. The atropisomers have significantly different polarities and the absorption coefficients of the longest wavelength absorption band that may differ by nearly one order of magnitude. In particular, the $\alpha_4$ isomer, with the four sulfamoyl substituents at the same side of the porphyrin plane, has the highest absorption coefficient and is the most amphiphilic of the atropisomers.

The widespread use of sulfonated chlorins and bacteriochlorins in PDT requires an economical and environmentally-friendly synthesis that can be performed on a industrial scale. It is a central object of the present invention to provide a new method for the preparation of such compounds based only on the precursor porphyrin and a hydrazide, where the latter is added in the solid state, heated above the melting temperature in a sealed reactor, in the absence of oxygen and base, and the desired product is obtained after some time.

It is also an object of the present invention to provide methods for PDT using topical administration of a said sulfonated chlorin or bacteriochlorin with a suitable vehicle. Vehicles for the topical administration of photosensitizers may take different forms, including liquid solutions, gels, creams, emulsions, ointments, etc. Typically, the formulation of such vehicles includes at least one surface penetration enhancer. Against the conventional wisdom in this field that drugs with molecular weights in excess of 500 Dalton do not permeate well through the skin [32], we provide formulations for the efficient intradermal delivery of said sulfonated chlorins or bacteriochlorins to skin disorders, where the said molecules attain molecular weights slightly in excess of 1 kD.

This invention relates to compounds for treatment and detection of hyperproliferative tissues such as tumors, using photodynamic methods. The compounds of the present invention are also useful for the treatment of dermatological disorders such as psoriasis, acne vulgaris and rosacea; gynecological disorders such as dysfunctional uterine bleeding; urological disorders such as condyloma virus; cardiovascular disorders such as restenosis and atherosclerotic plaques; photodynamic destruction of bacteria or viruses; hair removal and cosmetics; inhibition of immune responses following the transplant of organs or tissues.

Finally, it is a further object of the invention to provide methods for the diagnosis of hyperproliferative tissues using halogenated sulfonated chlorins or bacteriochlorins. Provided that these compounds preferentially accumulate in such tissues, the additional property required for diagnostic purposes is the unambiguous detection of very minute quantities of such compounds. These compounds have very distinct absorption bands in the red and infrared, where the tissues are most transparent. The selective excitation of these compounds leads to distinct fluorescence at wavelengths where biological molecules do not emit. The detection of fluorescence can be made with very sensitive equipment and sub-nanomolar quantities of halogenated sulfonated chlorins or bacteriochlorins can be measured in biological media. The source of irradiation for photodiagnosis and phototherapy is not restricted, but a laser beam is preferable because intensive light rays in a desired wavelength range can be selectively applied. It is necessary that the light rays have sufficient intensity to cause the compounds to emit fluorescence for diagnosis and to exert a cell killing effect for therapy. Additionally, when fluorinated sulfonated chlorins or bacteriochlorins are employed, fluorine-MRI (Magnetic Resonance Imaging) can detect the accumulation of these compounds in small regions of the body and follow the metabolites formed in its clearance form the body.

II. DETAILED DESCRIPTION

II. A. Definitions

As used herein, "hyperproliferative disorders" means those condition disorders sharing as underlying pathology excessive cell proliferation caused by unregulated or abnormal cell growth, and include uncontrolled angiogenesis. Examples of hyperproliferative disorders includes, but is not limited to cancers or carcinomas, myelomas, psoriasis, macular degeneration.

"Hyperproliferative tissue" as used herein means tissue that grows out of control and includes tumors and unbridled vessel growth such as blood vessel growth found in age-related macular degeneration.

As use herein, "tumor" denotes a neoplasm, and included both benign and malignant tumors. This term particularly includes malignant tumors that can be either solid or non-solid (such as leukemia). Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, head and neck cancer, cancer of the tongue, cerebral tumor, skin cancer, malignant goiter, prostatic cancer, colorectal cancer, cancer of the parotid gland, Hodgkin's disease, multiple myeloma, renal cancer, leukemia, and malignant lymphocytoma.

As use herein, "infecting agent" denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction.

As used herein, a "pharmaceutical agent" or "drug" refers to a chemical compound or composition capable of inducing a desired therapeutic or prophylatic effect when properly administered to a subject. It includes, but is not limited to photosensitizers that absorb light and use it either to act as a drug or to activate other chemical compounds that subsequently act as drugs.

As used herein, a 'pharmaceutically acceptable composition derivative' refers to compositions where the photosensitizers are bonded to biologically active groups, that is, any group that selectively promotes the binding, accumulation, or elimination in a particular biological environment. Examples known in the art include substituents derived from sugars, aminoacid derivatives, oligonucleotides, or ligands specific for receptors (steroid hormones, growth factors, neurotransmitters or antibodies). It also includes the salts of the photosensitizers.

As used herein, a "pharmaceutically acceptable carrier" includes any and all solvents, dispersion media, excipients to formulate tablets, pills, capsules, creams, solutions, suspensions or emulsions. It is well known in the art how to formulate these pharmaceutical compositions.

As used herein, a "surface penetration enhancer" refers to a chemical compound or composition capable of increasing or accelerating the transport of the drug across a barrier, such as the skin and other tissues, and including dimethylsulphoxide and other dialkylsulphoxides, dimethylformamide, dimethylacetamide, glycols, various pyrrolidone derivatives, Azone®, or any other of the skin-permeation assisting agents described in the literature, or mixtures thereof.

As used herein, "irradiation" means exposing a subject to all the frequencies of the electromagnetic spectrum. Preferably, the irradiation wavelength is selected to match the wavelength(s) where the drug absorbs light.

As used herein, "Luzitin" refers to any sulfonated tetrakisphenylchlorin or tetrakisphenylbacteriochlorin bearing electron-withdrawing groups in the ortho positions of the phenyl groups, and the following acronyms refer to specific chemical compounds that are non-limiting examples of this portfolio of molecules:

Luzitin-Cl-c is 5,10,15,20-tetrakis(2-chloro-5-sulfonylphenyl)chlorin,
Luzitin-FMet-c is 5,10,15,20-tetrakis(2-fluoro-5-N-methylsulfamoylphenyl)chlorin,
Luzitin-F is 5,10,15,20-tetrakis(2-fluoro-5-sulfonylphenyl)bacteriochlorin,
Luzitin-Cl is 5,10,15,20-tetrakis(2-chloro-5-sulfonylphenyl)bacteriochlorin,
Luzitin-$Cl_2$ is 5,10,15,20-tetrakis(2,6-dichloro-3-sulfonylphenyl)bacteriochlorin,
Luzitin-FMet is 5,10,15,20-tetrakis(2-fluoro-5-N-methylsulfamoylphenyl)bacteriochlorin,
Luzitin-$F_2$Met is 5,10,15,20-tetrakis(2,6-fluoro-3-N-methylsulfamoylphenyl)bacteriochlorin,
Luzitin-$Cl_2$Et is 5,10,15,20-tetrakis(2,6-dichloro-3-N-ethylsulfamoylphenyl)bacteriochlorin,
Luzitin-$Cl_2$Hep is 5,10,15,20-tetrakis(2,6-dichloro-3-N-heptylsulfamoylphenyl)bacteriochlorin,
Luzitin-$FMet_2$ is 5,10,15,20-tetrakis(2-fluoro-5-N,N-dimethysulfamoylphenyl)bacteriochlorin, Also used herein, are the acronyms
$Cl_2$PhB which is 5,10,15,20-tetrakis(2,6-dichlorophenyl) bacteriochlorin
BMPO which is 5-tert-butoxycarbonyl-5-methyl-1-pyrroline-N-oxide
DMPO which is 5-dimethyl-1-pyrroline-N-oxide
DMSO which is dimethylsulfoxide II. B. Precursor Compounds 5,10,15,20-tetrakis(halogenated-phenyl)porphyrins and 5,10,15,20-tetrakis(2-cyanophenyl)porphyrins, 5,10,15,20-tetrakis(2-trifluoromethylphenyl)porphyrins, 5,10,15,20-tetrakis(2-nitrophenyl)porphyrins and 5,10,15,20-tetrakis(2-carboxymethylphenyl)porphyrins were synthesized by the nitrobenzene method [33], mixing the pyrrol with the desired halogenated phenyl aldehydes in a mixture of acetic acid/nitrobenzene at 120° C. After cooling the pure porphyrin crystallizes directly from the reaction medium. All the characterization data (NMR, FAB, and micro-analysis) are in good agreement with previously described porphyrins.

Chlorosulfonation of the said porphyrins was carried out according to a method developed previously [34,35]. The required porphyrin (200 mg) and chlorosulfonic acid (10 mL, 150 mmol) were stirred at temperatures between 50 and 250° C. for 1 to 3 h. After this period, dichloromethane (200 mL) was added to the solution. A continuous water extraction was carried out, with stirring, until neutralization. The dichloromethane solution was then washed with sodium hydrogen carbonate and dried over anhydrous $Na_2SO_4$. Purification by column chromatography in silica gel using dichloromethane as eluent, and subsequent solvent evaporation, yielded the desired chlorosulfonated porphyrins as purple crystals.

Hydrolysis of the above chlorosulfonated porphyrins was conducted suspending 100 mg of the desired compound in distilled water (120 mL) and refluxing for 12 h. The resulting solutions were concentrated by rotary evaporation and the solid obtained was dried at 120° C. The sulfonic acid porphyrin derivatives were obtained with quantitative yields. Their characterization by NMR. FAB and micro-analysis, is good agreement with literature data [34,35].

II. C. Instruments

Absorption spectra were recorded on a Shimadzu UV-2100 spectrophotometer or with a Carry 50 Biospectrophotometer (Varian, Mulgrave, USA). Fluorescence spectra were measured with a Spex Fluorolog 3 spectrophotometer, with correction for the wavelength dependence system (RCA C31034 photomultiplier), or with a PerkinElmer LS 50 spectrofluorimeter. Transient absorption spectra were measured with an Applied Photophysics LKS 60 nanosecond laser flash photolysis kinetic spectrometer, using the third harmonic of a Spectra-Physics Quanta Ray GCR 130-01 Nd/YAG laser for excitation, a Hamamatsu 1P28 photomultiplier and a Hewlett-Packard Infinium oscilloscope (1 GS/s). Flash photolysis measurements were made in the presence of air and in argon saturated solutions. Photoacoustic calorimetry employed the same Nd/YAG laser, a home-made front-face photoacoustic cell with a 2.25 MHz Panametrics transducer (model 5676) and a Tektronix DSA 601 transient recorder [36]. Room-temperature singlet-oxygen phosphorescence was measured at 1270 nm with a Hamamatsu R5509-42 photomultiplier, cooled to 193 K in a liquid nitrogen chamber (Products for Research model PC176TSCE005), following laser excitation of aerated solutions at 355 nm, using an adapted Applied Photophysics spectrometer [37]. Singlet oxygen emission at 1270 nm was also monitored with a liquid nitrogen-cooled germanium detector (North Coast) coupled to a Tectronix Digitizing scope (TDS 520B), following sample excitation with 5 ns laser pulses of the third harmonic (355 nm) generated by a Q-switched Nd:YAG laser (Continuum Surelite II).

Elemental analyses were carried out on a Fisons Instruments EA 1108 CHNS-O elemental analyser. Melting points were measured on a Electrothermal capillary melting point apparatus. $^1$H-NMR and $^{19}$F-NMR and $^{13}$C-NMR spectra were recorded on a 300 MHz Brucker-Amx. $^1$H assignments were made using 2D COSY and NOESY experiments, while $^{13}$C assignments were made using 2D HSQC and HMBC experiments. MALDI-TOFMS data were acquired using an Applied Biosystems Voyager DE-STR instrument (Framingham, Mass., U.S.A.), which is equipped with a nitrogen laser ($\lambda$=337 nm).

Electron paramagnetic resonance (EPR) spectra of species with at least one unpaired electron were carried out using a Bruker ESP 300 spectrometer (IBM Instruments Inc.). Typical instrument setting were: microwave power 10 mW, modulation amplitude 0.8 G, sweep width, 60.0 G. The EPR spectra were recorded under in situ irradiation with a Hamamatsu diode laser. The following settings were employed to register the spectra: high power (4 mW), low modulation amplitude (0.2 G) and narrow scan range (60 G), and 20 scans were recorded fix each spectrum.

Irradiation in in vitro experiments was performed using either a halogen lamp or a laser source. In the first case, a 500 W halogen lamp was placed 50 cm from the irradiated plate to insure a homogeneous irradiation. A cooled water filter (d=35 mm) and a 600 nm cut off filter were placed between the lamp and samples. The fluence rate reaching samples was 3 mW/cm$^2$. The emission spectrum of the halogen lamp was recorded using a spectroradiometer IL2000 (Spectrocube), FIG. 1. In the second case, three Lynx external cavity diode lasers TEC 500 powered by PilotPC 500 Laser Controllers (Sacher Lasertechnik, Marburg, Germany) were employed. The laser energies were stable at 40 mW for the 748 nm laser, 10 mW for the 649 laser and 10 mW for the 633 laser. The laser energies were regularly measured with a Coherent LaserCheck. In some in vitro experiments, the laser light was focused on an optical fiber through a collimator in microbench, and delivered to the cells. This system reduced the 748 nm laser light to 30 mW.

The irradiation of bacteriochlorins in the photobleaching experiments employed the 748 nm Lynx diode laser. For animal studies we employed a costumer-made Hamamatsu diode laser, type LA0873. S/N M070301, which delivered 140 mW at 748 nm. This diode laser was controlled by a ThorLabs 500 mA ACC/APC Laser Diode Controller and in-house electronics. The laser energies of this and the other higher-energy lasers employed in this work were regularly checked with an Ophir model AN/2E laser power meter.

The time-dependent cellular uptake of the photosensitizers and the viability of the cells were confirmed by fluorescence microscopy using a Nikon ECLIPSE TS-100F instrument.

The fluorescence skin samples was analyzed with an Olympus Fluorescence Microscopy, model BX51M, using a U-MSWG2 fluorescence mirror unit (excitation filter 480-550, emission filter 590, dichromatic filter 570 nm). Confocal microscopy was performed with a Leica TCS SP5 (Leica Mycrosystems CMS GmbH, Mannheim, Germany) inverted microscope (DMI6000) with a 63' water (1.2 numerical aperture) apochromatic objective. Before turning to the confocal mode, the GUV suspension was directly observed using a sodium lamp as the light source, and a filter to select Rhod-DOPE fluorescence to evaluate yield of GUV formation. The excitation source in confocal fluorescence microscopy was either the 514 nm line from a Ar$^+$ laser, or the 745 nm line of a Ti:Sa laser. The emission was collected from 550 to 800 nm, taking advantage of the acoustic-optical tunable fiber and beam splitter of the Leica TCS SPC5 system. Stray light is minimized, in agreement with a "smart offset" that remained always below 0.5% (usually between −0.1% and 0.1%), and negligible photon counts outside the lipid structures. Confocal sections of thickness below 0.5 mm were obtained using the galvanometric motor stage. The 3D projections were obtained using the Leica Application Suite—Advanced Fluorescence software.

II. D. Methods

II.D.1. Partition Coefficients

The n-octanol:water partition coefficients (CP) were measured using a minor modification of the shake-flask method described by some of us in the literature [35]. The modification concerned the excitation of the absorption band ca 500 nm and the collection of the fluorescence in the red/IR region.

II.D.2. Photochemistry and Photophysics

Photobleaching experiments were conducted in PBS. PBS:methanol (50:50) and methanol solutions. The solutions were irradiated in a cuvette with an optical path of 1 cm and the Lynx diode laser. The initial absorption of the solutions was ca. 0.8. The mechanism of photobleaching was assessed with the irradiation of the sensitizer using the Hamamatsu diode laser at 80 mW. The sensitizer was irradiated in PBS and in the presence of ascorbic acid or azide.

Fluorescence quantum yields ($\Phi_F$) where determined in ethanol taking as reference the fluorescence quantum yield of $Cl_2PhB$ in toluene [4]. The absorptions of both reference and sample solutions were matched at ca 0.2 at the excitation wavelength of 515.5 nm, and the solutions were diluted by a factor 10 before collecting the fluorescence. The fluorescence quantum yield was obtained from the ratio of the fluorescence bands of the sample vs the reference, multiplied by the fluorescence quantum yield of the reference, 0.012 according to [12], after correction for the difference of refractive indexes of ethanol and toluene.

The triplet-triplet absorption spectra and the triplet lifetimes of the photosensitisers ($\tau_T$) were measured with the transient absorption spectra equipment described above, with excitation at 355 nm, where the solutions had absorbances between 0.25 and 0.30.

Time-resolved photoacoustic calorimetry (PAC) was made with the set-up described above using a procedure described by some of us [4]. All the measurements were made in ethanol using Manganese 5,10,15,20-tetraphenylporphyrin as photoacoustic reference.

Singlet oxygen quantum yields in ethanol were obtained using a procedure described by some of us [37], using phenalenone as reference. The literature value for the singlet oxygen quantum yield obtained with phenalenone in ethanol is $\Phi_\Delta$=0.95 [38].

II.D.3. Electronic Paramagnetic Resonance (EPR)

Reactive oxygen species produced by irradiation of photosensitizers in PBS, namely the superoxide ion and the hydroxyl radical, form adducts with various spin traps. Such adducts can be identified by EPR. The PBS buffer employed in these measurements was previously treated with chelating resin, Chelex 100, in order to remove any contaminating metal ions that may catalyze decomposition of peroxides. Two spin traps were employed: BMPO and DMPO. DMPO was first purified with activated charcoal/benzene, and then a 1.0 M stock concentration was determined spectrophotometrically using $\epsilon_{226}$=7200 M$^{-1}$ cm$^{-1}$. EPR measurements were performed at room temperature using the Bruker spectrometer described above, with in situ irradiation with the Hamamatsu diode laser.

II.D.4. Skin Permeation Tests

The best animal model to test skin permeation is the minipig, in view of the similarities between minipig and human skin characteristics [39]. Different formulations of creams, ointments, gels and liquid solutions were employed to enhance the permeation of the photosensitizer through skin samples of minipigs. The formulations incorporated the photosensitizers in quantities varying from 0.1 to 10%, permeation enhancers such as Azone® and DMSO, and various excipients. Ex vivo tests employed skin excised from the back of the minipigs. In vivo tests were made on the back of the minipigs. In each test the formulation was applied in area ca. 1 cm² of skin for the desired amount of time, under occlusive dressing. Once that time had elapsed, the formulation was removed with a spatula and washed with medical cotton embedded in ethanol, until no traces of the sensitizer could be seen in the medical cotton. In the in vivo tests, the skin samples were surgically removed and the animals were then sacrificed.

The first step of the procedure for tissue fixation of the skin samples was immersion in paraformaldehyde (4% in aqueous solution) for at least 24 h. Next, the samples were transferred to a 25% sucrose solution for at least 48 h. Following this treatment, the skin samples become denser than the sucrose solution. An aliquot was extracted with a biopsy punch, frozen in dry ice and then mounted in holder with Tissue-Tek O.C.T. Compound (Sakura Finetek Europe B.V., Zoeterwoude, The Netherlands) and cut in slices with controlled thicknesses selected between 25 and 100 mm in a cryostate. The skin slices were collected in microscope slides and kept refrigerated until they were analyzed by fluorescence microscopy and confocal microscopy. Alternatively, rather than using paraformaldehyde as a fixative, the skin samples were directly frozen in dry ice.

II.D.5. In Vitro Experiments

The drugs described herein have been evaluated in in vitro studies. One set of in vitro studies employed irradiation with a halogen lamp equipped with several filters. The other set employed diode laser irradiation to deliver the light to each cell culture.

II.D.5.i) In Vitro Experiments with Halogen Lamp Irradiation

The cell lines employed in halogen lamp irradiation were the MCF7 (human breast carcinoma), SKMEL 188 (human melanoma) and S91/I3 (mouse melanoma) cells. They were used both for cytotoxicity and photocytotoxicity experiments. MCF7 cells were grown supplemented with 10% fetal calf (FBS) serum, 25 units/ml of penicillin, and 25 µg/ml of streptomycin. Human melanoma cells SKMEL-188 were grown in F10 medium supplemented with 10% fetal calf serum (FCS), 100 units/ml of penicillin, and 100 µg/ml of streptomycin. I3 subline of Cloudman S91 melanoma cells were cultured in RPMI 1640 medium supplemented with 100 units/ml of penicillin, 100 µg/ml streptomycin and 5% fetal calf serum (FCS) (Gibco BRL). All cell lines were cultivated as monolayer in Petri dishes of 60 mm diameter and incubated at 37° C. in a humid atmosphere containing 5% $CO_2$.

Cytotoxicity. Cell metabolic efficiency and viability were determined by the uptake and reduction of 3-(4,5-dimethylthiazol-2-yl)-2,5-diphenyl tetrazolium bromide (MTT) to an insoluble formazan dye by cellular microsomal enzymes. The cell lines were grown in RPMI medium with 10% fetal calf serum, penicillin and streptomycin. Cells were maintained in 5% $CO_2$, 95% air and 100% humidity. For determining cytotoxicity, these cells were plated in 96-well plates at a density of 1×10⁴ cells well in complete media. After 24 h, the cells were incubated with photosensitizers at different concentrations (0.25 up to 50 µM) for 18 hours at 37° C. The cells were then washed twice with PBS and incubated in growth medium at 37° C. for 24 h. Next, the medium was replaced by 100 µl of fresh medium and 20 µl of MTT, and the cells were incubated with MTT for 3 h, with a final concentration of 0.5 mg/ml. Then the culture medium was replaced with DMSO-methanol solution (1:1) to dissolve the blue formazan crystals. The 96-well culture plate was shaken for 0.5 min at room temperature and immediately read for optical density at 560 nm using an ELISA reader (GENios Plus; Tecan Trading AG, Switzerland). The cell survival was expressed by the absorbance changes of the formazan salt, and survival rate was given as the percent ratio of viable treated cells vs. the number of viable untreated cells. Number of cells was determined from linear regression of a calibration curve.

Time-Dependent Cellular Uptake. SKMEL 188, S91 and MCF7 cells were seeded on 96-well plates at 1×10⁴ cells per well and exposed to 20 µM concentrations of chlorins and bacteriochlorins photosensitizers in PBS for various time intervals, from 10 min up to 180 min to probe time-dependent drug accumulation. At the end of the incubation interval, the cells were washed three times with PBS and re-suspended in 100 µL of 0.25% Triton X-100 in PBS. The retention of cell-associated photosensitizers was detected by fluorescence measurement of the accumulated photosensitizers using an ELISA reader. In addition, the uptake of photosensitizer and the viability of the cells were confirmed by fluorescence microscopy. In these experiments, SKMEL 188. S91 and MCF7 cells were incubated for 2 hours with 20 µM of photosensitizer, followed by washing the cells three times with PBS, re-suspension in PBS and examination by fluorescence microscopy.

Cell photosensitization. SKMEL 188, S91 and MCF7 cells were prepared as described above. On the basis of cytotoxicity assays, a 5 µM concentration of photosensitizer was selected for the photosensitization assays. The cells were incubated for 12 h at 37° C. and then irradiated at a 0.53 mW cm² fluence rate and in doses ranging from 0.1 to 0.64 J cm². We recall that photosensitizer uses only ca. ⅕ of the available fluence rate of the filtered halogen lamp. The MTT test was performed 24 h after irradiation. The values were obtained from three independent experiments and expressed as percent of cell survival with reference to control cells, which were manipulated in the same manner but without incubation with photosensitizer and without illumination.

II.D.5.ii) In Vitro Experiments with Laser Irradiation

The cell lines employed in laser irradiation were the HT-29 (human colon carcinoma), PC-3 (human prostate carcinoma), SW2 (human small cell lung cancer), A-549 (human non-small cell lung cancer). S91/I3 (mouse melanoma) and CT26 (mouse colon carcinoma). They were used both for cytotoxicity and photocytotoxicity experiments. PC-3. SW2 and S91I13 cells were cultured in RPMI-1640 medium (Sigma-Aldrich, Steinheim, Germany) and HT-29, A-549 and CT26 cells were cultured in Dulbecco's Modified Eagle Medium (DMEM) (Cambrex Bioscience, Verviers, Belgium). Both cell culture mediums were supplemented with 10% heat-inactivated Fetal Bovine Serum (FBS) (Cambrex Bioscience, Verviers, Belgium) and 100 IU/ml penicillin-100 µg/ml streptomycin (Cambrex Bioscience, Verviers, Belgium). The DMEM medium used for CT26 cells was also supplemented with HEPES 10 mM. Cell lines were maintained in 75 cm² flasks (Orange Scientific, Braine-l'Alleud, Belgium) at 37° C. in humidified atmosphere with 5% $CO_2$. For the in vitro studies, cells at 85-90% confluence, were detached with Trypsin-Versene-EDTA solution (Cambrex Bioscience, Verviers, Belgium), counted and seeded in flat-bottom 96-well plates at the desired densities.

Cell viability assay. In the end of the experiences cell viability was evaluated by the resazurin reduction assay [40]. Briefly, resazurin (Sigma-Aldrich, Steinhelm, Germany) stock solution (0.1 mg/ml in phosphate buffer saline (PBS) pH 7.4) was diluted 10% in culture medium without FBS or antibiotics and 200 µl were added to the cells in each well. Plates were incubated for 3-4 h at 37° C. The absorbance values of each well were measured at 540 nm and 630 nm using a microplate reader Multiskan Ex (Thermo-Electron Corporation, Vartaa, Finland).

Cytotoxicity. Cells were seeded in flat-bottom 96-well plates (Orange Scientific, Braine-l'Alleud, Belgium) in 100 µl of culture medium and were allowed to adhere overnight. The photosensitizer was added to the cells (diluted in 100 µl culture medium) at final concentrations between 0.01 and 1 mM. Each concentration was tested in quadruplicate. The incubation periods in the dark at 37° C. were two times the doubling time for the tested cell line. After the incubation the cell viability was evaluated. In parallel control experiments, cells were incubated without the drug. Cytotoxicity was quantified by expressing cell death relatively to untreated cells (% of control cells). The results were plotted as dose response curves (% of cell death as a function of the concentration of the DRUG), which allow the determination of the concentration that inhibit 50% of cell growth ($IC_{50}$).

Cell photosensitization. Cells were seeded in DB Falcon black 96-well plates with clear flat-bottom (DB Biosciences—Labware, N.J., USA) in 100 µl of culture medium and were allowed to adhere overnight. The drug was added to the cells (diluted in 100 µl culture medium) in order to obtain the desired concentration. Cells were incubated with the drug in the dark at 37° C. for a given period of time. This period of incubation is usually referred as drug-to-light interval. After incubation cells were washed once with 200 µl of PBS to remove the non-internalized drug and 100 µl of fresh culture medium was added. Cells were irradiated (each well individually) with the 748 nm light of the Lynx diode laser described above, at a power of 100.7 mW/cm². The irradiation time was chosen in order to obtain the desired light dose. Two parallel control conditions were tested: cells were incubated in the dark with the highest dose of drug and were not irradiated, and cells were irradiated with the highest light dose without drug. After the irradiation 100 µl of fresh culture medium was added. Cell viability was evaluated approximately 24 h after the irradiation.

II.D.6. In Vivo Experiments

The mice used in the present study were form two sources. Dark toxicity, biodistribution and farmacokinetic studies employed DBA/2 mice, weighing 20-30 g, from the animal breeding facility at the Faculty of Biochemistry, Biophysics and Biotechnology, Jagiellonian University, Krakow. The mice were kept on a standard laboratory diet with free access to drinking water. The use of such animals for experimental purposes was approved by the Jagiellonian University Committee for Ethics of Experiments on Animals (decision No. 384/99). Such mice were also employed in PDT.

The other mice were Balb/C weighing 20-25 g, from the animal breeding facility of Charles River Laboratories (Barcelona). The mice were kept on a standard laboratory diet with free access to drinking water. The use of such animals for experimental purposes was approved by the Board of Centro de Neurociências e Biologia Celular (Coimbra).

The four minipigs used in the present study were obtained from IMIDRA (Instituto Madrileño de Investigación y Desarrollo Rural, Agrario y Alimentario)—Aranjuez (Madrid). They were all females, aged 6-8 months, white with brown spots, average weight 56.8 kg (66.2, 57.1, 43.5, 60.6 kg). They were received at Estação Zootécnica Nacional, Vale de Santarém, where they were accommodated in individual boxes with 1.5 m², feed with a standard diet for pigs and water ad libidum, for an acclimation period of three weeks. The study was performed in accordance to the Portuguese ethical guidelines on a license granted by Direcção de Serviços de Saúde e Protecção Animal, ref. 0420/000/000/2007. Access to food was suspended 24 h hours before treatment. The backs of the animals were shaved 24 h prior to the application of the formulations. The topical administration of photosensitizers was done under anesthesia. The pre-medication employed 30 min in advance was: Azaperone (Stresnil®—Veterinaria ESTEVE—Spain), 2 mg/kg intramuscular injection+atropine sulphate, 50 mg SC. The induction was done with ketamine (Clorketam®—Vétoquinol, France), 20 mg/kg, intramuscular injection. The anesthesia was maintained with endotracheal intubation, using spontaneous ventilation with 2-3 l/min of oxygen+3% isoflurane (Isoflo®—Veterinária ESTEVE, Spain). The samples were collected from 3 minipigs under the anesthesia described above. Skin aliquots with sizes 20×20×10 (length, side, depth) were obtained by surgical excision. After the collection of the skin samples, the animals were then killed with an overdose of sodium thiopental (25 mg/kg)+20 ml of 7.5% potassium chloride. The fourth minipig was followed by 3 weeks while feed with a standard diet for pigs and water ad libidum. After 3 weeks, the topical administration of photosensitizers was performed again under anaesthesia. The animal was rendered unconscious by electrical shock and killed by jugular venesection.

II. E. Properties of the Compounds

II.E.1. Physical Properties

As mentioned in the Background, the most important physical and chemical properties of the drugs relevant for PDT are a strong absorption in the 600-800 nm range, high efficiency of singlet oxygen generation, chemical stability, controlled photobleaching and octanol:water partition coefficients between −2 and 5. These properties meet the desired light absorbance in the phototherapeutic window, the efficient photogeneration of cytotoxic species, reduce side effect such as prolonged skin photosensitivity, and facilitate systemic or transdermal administration routes.

The absorptivities of the compounds were measured at several concentrations, from 1 to 20 µM, and in all cases were observed to follow the Beer-Lambert law. Additionally, the wavelength of maximum absorption ($\lambda_{max}$) in the infrared did not vary in the concentration range studied. This is indicative of little aggregation between the molecules, which exist mostly as monomers at these concentrations in the solvents studied. Table 1 presents typical red and infrared molar absorption coefficients ($\epsilon_{max}$) and wavelength maxima. The same table also presents representative fluorescence quantum yields ($\Phi_F$) of Luzitins. The fluorescence quantum yields decrease of these molecules decrease in the presence of chlorine substituents, a fingerprint of the heavy atom effect expected for such molecules.

The triplet-triplet absorption spectra of the Luzitins measured in this work were in good agreement with that in the literature data for chlorins and bacteriochlorins. All triplet decays were clearly mono-exponential. In de-aerated solutions, produced by flushing $N_2$ for at least 30 min, the triplet lifetimes ($\tau_T$) are in the millisecond range, demonstrating inefficient photochemistry in the absence of oxygen. Representative values are given in Table 1. In air-saturated ethanol the triplet lifetimes dropped to a 200-300 nanoseconds, significantly shorter than the lifetimes of the corresponding porphyrins. Such values are consistent with diffusion limited energy transfer from the triplet state of the sensitizer to molecular oxygen through a charge-transfer interaction.

All the singlet oxygen emissions measured in aerated ethanol solutions are very well described by mono-exponential decays, with typical singlet oxygen lifetimes ($\tau_\Delta$). The $\Phi_\Delta$ values of Table 1 were obtained by the procedures described above and are representative of these photosensitisers.

TABLE 1

Fluorescence quantum yields, triplet lifetimes, singlet oxygen quantum yields and singlet oxygen lifetimes of representative photosensitizers in air-saturated ethanol solutions.

| | $\lambda_{max}$ (nm) | $\epsilon_{max}$ (M$^{-1}$ cm$^{-1}$) | $\Phi_F$ | $\tau_T$ (air) (nsec) | $\Phi_\Delta$ | $\tau_\Delta$ (μsec) |
|---|---|---|---|---|---|---|
| Photofrin® | 630 | 3,200 | | 400[a] | [b] | 10.6[a] |
| Luzitin-Cl-c[c] | 650 | 7,000 | 0.039 | — | 0.69 | — |
| Luzitin-Cl | 746.5 | 23,000[d] | 0.0403 | 240 | 0.43 | 13.6 |
| Luzitin-Cl$_2$ | 745.0 | 27,000[d] | 0.0062 | 226 | 0.85 | 15.4 |
| Luzitin-FMet | 742.5 | 62,000[d] | 0.0589 | — | 0.71 | 14.1 |
| Luzitin-F$_2$Met | 742.5 | 78,000[d] | — | — | — | — |
| Luzitin-Cl$_2$Et | 745.5 | 96,000 | 0.0081 | 265 | 0.66 | 13.7 |
| Luzitin-Cl$_2$Hep | 746 | 75,000 | 0.0082 | 295 | 0.63 | 14.3 |
| Luzitin-FMet$_2$ | 742.5 | 78,000[d] | 0.0585 | — | — | — |
| Foscan® | 650 | 29,600[e] | 0.089[f] | | 0.43[f] | |

[a][41].
[b]HpD monomer units have $\Phi_\Delta$ = 0.64 in methanol but in water it is mostly present in the form of dimers with $\Phi_\Delta$ = 0.11 [42].
[c]In aqueous solution.
[d]Corrected for the chlorin content.
[e][43].
[e]In methanol, but drops to half this value in 65% water in methanol [44].
[f]In methanol [45].

Typically, the sum of the fluorescence and singlet oxygen quantum yields of Luzitins is 0.6-0.8, and 20 to 40% of the light absorbed in used for other processes. These processes were investigated with time-resolved photoacoustic calorimetry (PAC) and electron paramagnetic resonance (EPR). PAC measures the amount of energy released by radiationless processes (internal conversion, intersystems crossing, chemical reactions) in the decay of the electronically excited states. EPR measures the amount of species with unpaired electrons (free radicals) present in the sample, and was employed here under direct laser irradiation to measure the photoinduced generation of superoxide ion, hydroxyl radical and other reactive oxygen species (ROS). The energy release measured by PAC is consistent with the formation of bacteriochlorin triplet states with nearly unit quantum yields and triplet energies of 105-125 kJ/mol, consistent with literature data on halogenated bacteriochlorins [12]. EPR spectra collected during the irradiation of Luzitins in PBS and in the presence of DMPO and BMPO revealed the presence of superoxide ion and hydroxyl radical. Together, the EPR and PAC data show unambiguously that irradiation of these photosensitizers at 748 nm leads to the formation of superoxide ion and, subsequently, of hydroxyl radical, which contribute to the phototoxicity of Luzitins. Thus, the phototoxicity of the sensitizers is higher than that anticipated from their singlet oxygen quantum yields, which are already 5 times higher than that of Photofrin®.

The chemical stability of the compounds was studied exposing them to light, air, and pH changes. The most significant degradation occurs for aerated solutions irradiated by light of the appropriate wavelength. In such circumstances the photobleaching of the compounds follows a first-order rate and is proportional to the energy of the incident laser light. In general, it was also observed that the photobleaching rate increases with the amount of water present in the solution. Bennett reported the photoconversion of Foscan® (m-THPC) and of the analogous bacteriochlorin (m-THPB) in PBS:methanol (50:50) [46]. Scherz reported the photoconversion of Tookad® in acetone and Triton-X:PBS [3]. For the purpose of comparing the photostability of Luzitins with that of Foscan® and Tookad®, we present in Table 2 the half-lives ($t_{1/2}$) of representative drugs described herein, together with those of Foscan and Tookad® normalized for a laser power of 100 mW.

TABLE 2

Half-lives of bacterioclorins under 100 mW laser irradiation at 748 nm, and their n-octanol:water partition coefficients ($K_{OW}$).

| Drug | solvent | $t_{1/2}$ (sec) | log $K_{OW}$ |
|---|---|---|---|
| Tookad®[a] | Surfactant:PBS | 1.56 | |
| Luzitin-F | PBS | 58 | — |
| Luzitin-Cl | PBS | 174 | −1.70 |
| Luzitin-Cl$_2$ | PBS | 358 | −1.75 |
| Luzitin-FMet | PBS:methanol | 647 | 2.3 |
| | methanol | 3,553 | |
| Luzitin-F$_2$Met | PBS:methanol | 6,480 | 2.7 |
| Luzitin-Cl$_2$Et | PBS:methanol | 4,013 | 1.8 |
| Luzitin-FMet$_2$ | methanol | 4,352 | >4 |
| Foscan®[b] | PBS:methanol | 8,582 | |
| Luzitin-Cl$_2$Hep | methanol | 164,105 | >4 |

[a][3].
[b][46].

We distinguish the photobleaching of our bacteriochlorins from the photoconversion of m-THPB or Tookad®. This distinction is based on the fact that after prolonged laser irradiation most of our bacteriochlorins are transformed into products that do not have a detectable visible absorption, and can appropriately be described as photobleaching. On the other hand, the laser irradiation of m-THPB or Tookad® produces large amounts of the corresponding chlorins, that do not absorb the same laser light, and this is more appropriately described as a photoconversion into another dye. The photobleaching of our bacteriochlorins is advantageous because it leads to less skin photosensitivity, as opposed to the photoconversion to another dye.

II.E.1. Biological Properties

Photofrin® provides important benchmarks for dark toxicity and PDT efficacy in vitro. The toxicity of Photofrin® in the dark towards the non-small cell lung cancer cell line H1299 was evaluated for several Photofrin® concentrations and the cell viability decreased to 50% for IC$_{dark50}$=8.0 μg/ml [47]. A similar study on the dark toxicity of Photofrin® towards Colo-26, a murine colon carcinoma cell line, gave IC$_{dark50}$≈20 μg/ml (30 μM, assuming a monomer) [48]. The human adenocarcinoma (HT29) cell line has been one of the most widely studied cell lines in PDT. The concentration-dependence studies of Photofrin® in HT29 cells gave the lethal dosage of 50% killing under 5 J/cm$^2$ filtered halogen light of IC$_{50}$=7.5 μg/ml. For 90% killing the concentration raises to IC$_{90}$=40 μg/ml [49]. For the same cell line, Foscan® is much more phototoxic with IC$_{50}$=0.8 μg/ml when a dye laser at 650 nm is used to deliver 10 J/cm$^2$; however, for this light dose, IC$_{90}$>10 μg/ml and falls within the limits of its dark toxicity, IC$_{dark50}$=13 μg/ml [50]. As opposed to Photofrin®, the molecular composition of Foscan® is known and it is more convenient to express its ICs in molar units. In these units, the dark cytotoxicity of Foscan® is IC$_{dark50}$=19 μM, and the toxicity for a light dose of 10 J/cm$^2$ is IC$_{50}$=1.2 μM. Finally, it is interesting to refer that Tookad® causes a 50% death rate in HT29 cells for a dose of 48 µM under an irradiation of 25 J/cm² (patent US2003/6,569,846). Although the values of $IC_{50}$ and $IC_{90}$ depend on modes of administration, incubation times, light fluences and other details of the experiments, the values given above are indicative of the best practice in this field.

Table 3 compares the dark toxicity of Photofrin® and Foscan® with that of Luzitins. Using the methods described above and further detailed in the examples below, the light doses required to kill 50% and 90% of several cell lines under filtered halogen light in the presence of a halogenated and sulfonated chlorin are presented in Table 4, and the corresponding values for a halogenated and sulfonated bacteriochlorin are presented in Table 5. Table 6 presents the phototoxicity in terms of the concentration of various Luzitins required to kill 90% of the cells under a laser light dose of 6 J/cm².

TABLE 3

Dark toxicity of photosensitizers in human and murine cancer cell lines.

| Cell line | Incubation time (h) | Photofrin ® $IC_{50}$ (µg/ml) | Foscan ® $IC_{50}$ (µM) | Luzitin-Cl[a] $IC_{50}$ (µM) |
|---|---|---|---|---|
| H1299 | | 8.0 | — | — |
| HT-29 | 48 | — | 19 | 500 |
| SW2 | 48 | — | — | 400 |
| PC-3 | 72 | — | — | 600 |
| S91I3 | 40 | — | — | 500 |

[a]Cells were incubated for two times the population DT in complete culture medium, in the dark, in the presence of varying concentrations of the photosensitizer.

TABLE 4

Light doses, in J/cm², required to kill 50% and 90% of the cells in the cell lines indicated, for [Luzitin-Cl-c] = 20 µM (≈20 µg/ml) under filtered halogen lamp irradiation.

| Cell line | S91 | SKMEL 188 | MCF7 |
|---|---|---|---|
| $LD_{50}$ | 0.13 | 0.26 | 0.3 |
| $LD_{90}$ | 0.26 | 0.46 | 0.7 |

TABLE 5

Light doses, in J/cm², required to kill 50% and 90% of the cells in the cell lines indicated, for [Luzitin-Cl] = 20 µM (≈20 µg/ml) under filtered halogen lamp irradiation.

| Cell line | S91 | SKMEL 188 | MCF7 |
|---|---|---|---|
| $LD_{50}$ | 0.15 | 0.1 | 0.08 |
| $LD_{90}$ | 0.3 | 0.32 | 0.25 |

TABLE 6

The concentration of sensitizer, in µM, required to kill 90% of cells human prostate carcinoma (PC-3), human adenocarcinoma (HT-29), human non-small cell lung carcinoma (A-549), mouse melanoma (S91I3), and murine colon carcinoma (CT26) cell lines under 6 J/cm² diode laser irradiation at 28.5 mW.

| Photosensitizer | PC-3 | HT-29 | A-549 | S91I3 | CT26 |
|---|---|---|---|---|---|
| Luzitin-Cl$_2$ | 20 | 50 | — | 40 | — |
| Luzitin-Cl$_2$Et | 5 | 10 | 10 | — | 5 |
| Luzitin-FMet | 0.5 | 0.5 | 0.5 | — | 1.0 |
| Luzitin-F$_2$Met | 0.5 | — | 0.5 | — | 1.0 |

Tables 4-6 show the low dark toxicity of Luzitins and their very high phototoxicity. Table 6 shows that the Luzitin concentrations required to kill 90% of the cells in various cell lines are up to 100 times smaller than those required by Photofrin®, and up to 20 times smaller than those required by Foscan®. With laser light doses of 6 J/cm² (60 seconds irradiation in our experimental conditions) it was possible to kill 100% of the cells in any of the cell lines studied with Luzitin concentrations of negligible cytotoxicity in the dark.

II. F. Methods of Use of the Compounds and Compositions

Luzitins may be administered by topical, oral, intravenous, subcutaneous, intraperitoneal, rectal, sublingual, nasal, ocular, ear or inhalation formulation, depending on the clinical situation. The pharmaceutical formulation is adapted to the chosen route of administration. The formulations comprise besides the Luzitins (individually or in combination with each other), a pharmaceutically acceptable carrier. The Luzitins may be derivatized as the corresponding salts, esters, enol ether or esters, acetals, ketals, orthoesters, hemiacetals, hemiketals, acids, bases, solvates, hydrates or prodrugs prior to formulation.

Following topical or systemic administration, or both, the area treated is exposed to light of the appropriate wavelength, preferably between 630 and 690 nm for chlorins or between 720 and 780 nm for bacteriochlorins, and most preferably using a laser. Methods of irradiating various areas of the body are well known in the art. The drug-to-light interval may range from a few minutes to several days, depending on the mode of administration. The light dose depends on the administration route, light source and therapeutic target. For continuous laser irradiation, the light dose should be between 10 and 250 Joules/cm², with a laser power between 20 and 200 mW/cm². It is also possible to use pulsed laser irradiation with energies per pulse between 0.001 and 10 ml/cm². The light dose may be applied in one or several sessions. For diagnostic purposes, the light dose may be reduced. When broadband light sources are employed in the irradiation, the light doses are increased to maintain the energy of the light source in the spectral regions where the Luzitin absorbs, at the level prescribed for laser irradiation.

The Luzitins may be administered at once, or may be divided into a number of smaller doses to be administered at intervals of time. Luzitins may be administered in conjunction with other medicaments to obtain synergistic effects. The light doses administered after the drug-to-light interval fall in the ranges given above for a single dose. The treatment may be repeated several times at various time intervals. It is understood that the precise dosage and duration of the treatment is a function of the disease being treated and may be determined empirically using protocols known in the art.

II.F.1. Systemic Administration (Oral, Injectables, Aerosols, Rectal)

A common limitation associated to oral administration is the putative digestion of the drug under the acidic conditions found in the stomach. As shown in an example below, Luzitins are relatively stable at pH 1 for 3 hours. The spectral changes observed at low pH are due to the protonation of the pyrrole ring, but are reversed when the acidity are neutralized. Another difficulty frequently encountered in oral administration is that of bioavailability. It is possible to make Luzitins that come close to meet Lipinsky rule of five [51] for intestinal absorption. Luzitins can have log $K_{OW}$<5, 4 hydrogen bond donors, 12 hydrogen bond acceptors and molecular weight of 1 kD. Only this last parameter significantly exceeds the limits of the above-mentioned rule.

Taking into account the physical-chemical properties of Luzitins, both solid, semi-solid and liquid dosage forms can be considered. In this regard, the state-of-the-art in terms of pharmaceutical adjuvants for the various pharmaceutical dosage forms and modes of administration should be considered.

The preferred drug-to-light interval in systemic administration may range from a few minutes to 3 days, depending on the mode of administration. The pharmaceutical compositions should provide a dosage from 0.01 mg to 100 mg of Luzitin (or combination of Luzitins) per kilogram of body weight per day. The preferred daily dose of Luzitins is between 0.1 and 10 mg per kilogram of body weight.

II.F.2. Topical Administration

Topical administration can be achieved with appropriate formulations containing one or various surface penetration enhancers and other excipients in the form of liquid, gel, hydrogel, cream, ointments, sprays or any other acceptable dermatological formulation. As mentioned in the Background, the skin permeation achieved for Photofrin® or other large molecular mass photosensitizers is insufficient for efficient PDT of skin disorders. Luzitins also fail to meet most of the criteria for good transdermal delivery [32]. However, our ability to modulate the amphiphilicity and hydrogen bonding ability of these compounds and, to a certain extent, their molecular mass, simplifies the task of finding formulations that promote their passive diffusion to the dermis. A gel formulation presented in Example 21, is shown to produce fast and efficient topical delivery to the dermis.

The preferred drug-to-light interval in topical administration is between 15 min and 3 h. The formulation should contain 0.01 to 10% the Luzitin. In a preferred embodiment, the percentage of the sensitizer in the formulation is between 0.1 and 1%.

Topical administration also contemplates application to the eye. Applications intended for ophthalmic use may be formulated as 0.01%-10% isotonic solutions, pH 5-7, with appropriate salts.

This invention will now be described in more detail in the following non-limiting Examples, with reference to the drawings in which:

FIG. 1. Spectral density of the 500 W halogen lamp with a 600 nm cut-off filter and infrared absorption spectrum of a chlorin (dotted line) and of a bacteriochlorin (dashed line).

FIG. 2. Absorption spectrum of Luzitin-FMet-c obtained from the reduction of the corresponding porphyrin in a synthetic route characterized by the total absence of organic solvent and bases.

Figure 3:
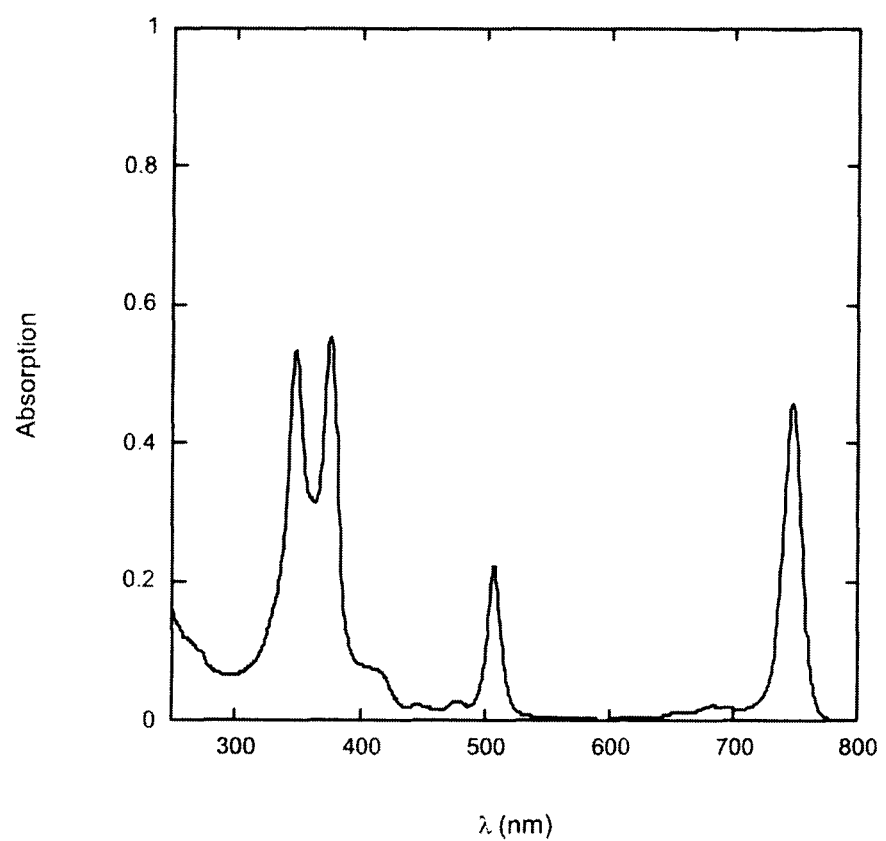

FIG. 3. Absorption spectrum of Luzitin-$Cl_2$Et obtained from the reduction of the corresponding porphyrin in a synthetic route characterized by the total absence of organic solvent and bases.

Figure 4:
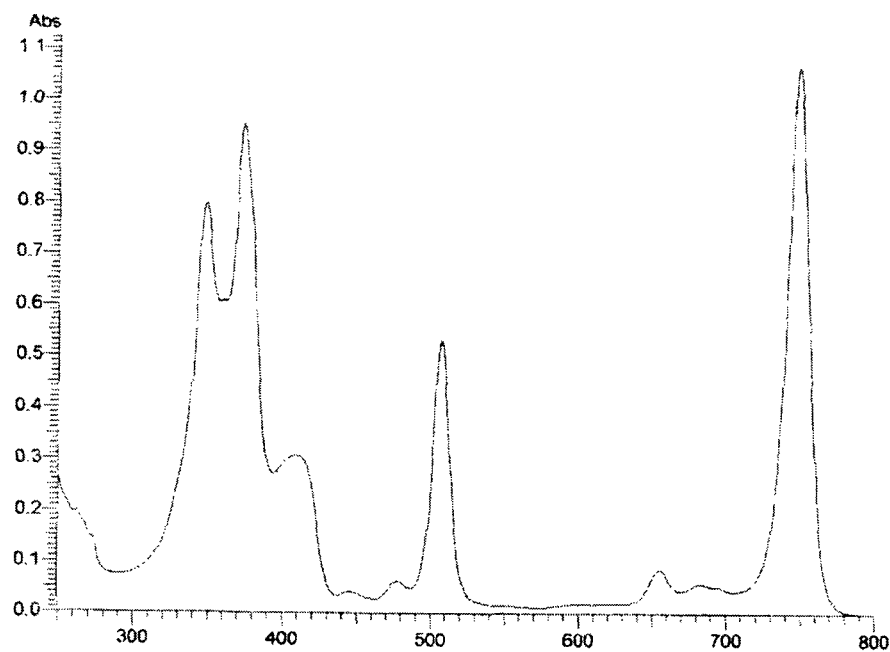

FIG. 4. Absorption spectrum of the more polar fraction ($\beta\alpha_3+\alpha_4$) of atropoisomers of Luzitin-$Cl_2$Et illustrating the increased absorptivity in the infrared, estimated to reach $\epsilon_{max}=150,000$ M$^{-1}$ cm$^{-1}$ at 748 nm.

Figure 5:
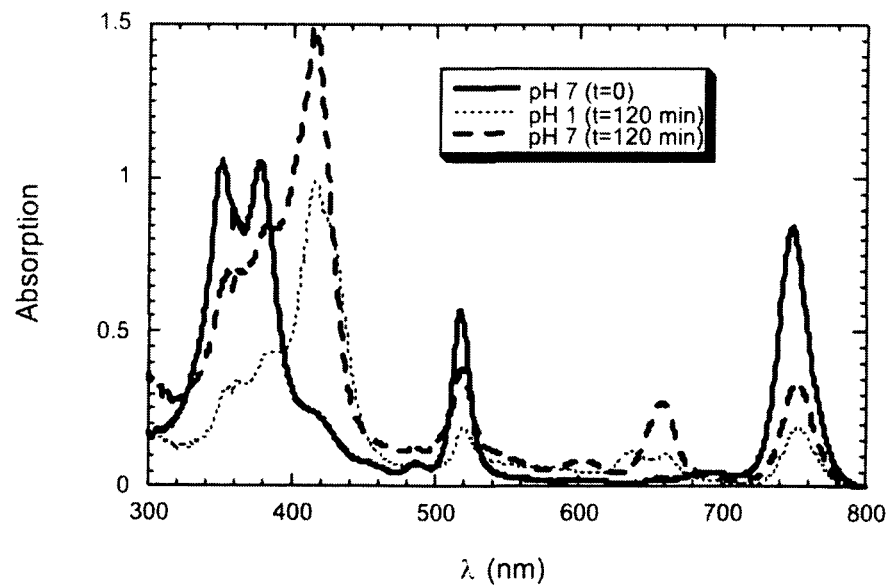

FIG. 5. Absorption spectrum of Luzitin-$Cl_2$ in neutral aqueous solution (full line), after 2 hours at a pH of 1 (dotted line) and after neutralization (dashed line). The spectra were corrected for the dilution effect produced by the drop wise addition of HCl and NaOH in aqueous solution.

Figure 6:
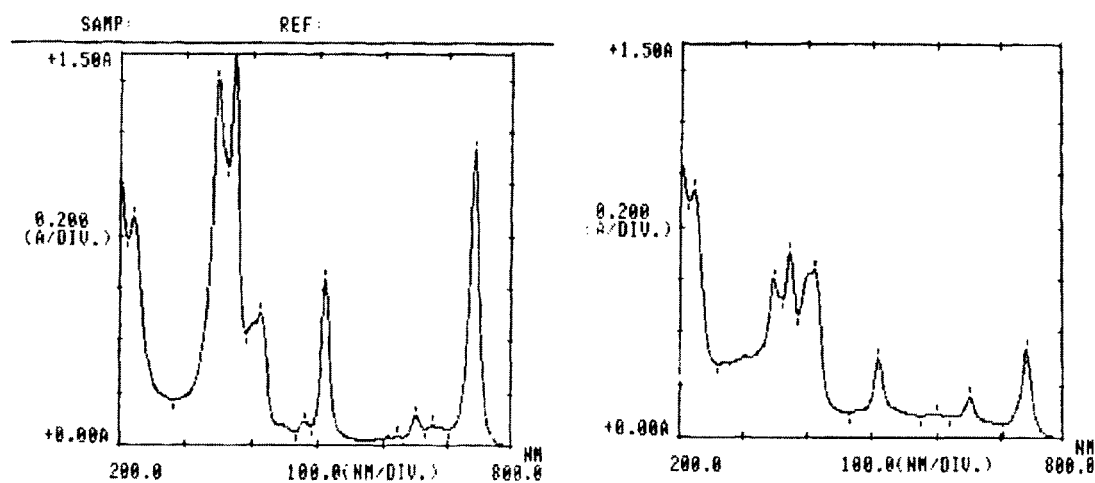

FIG. 6. Absorption spectra of Luzitin-FMet in PBS: methanol (3:2) before (left) and after (right) 65 min irradiation with the 748 nm Lynx diode laser at 28.8 mW (110 J), illustrating controlled photobleaching.

Figure 7:
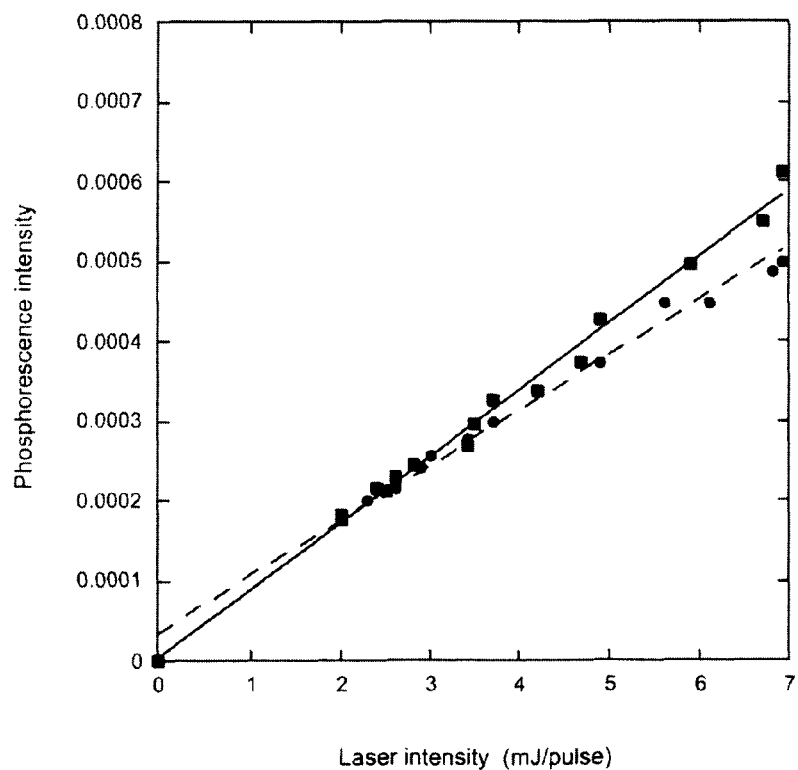

FIG. 7. Singlet oxygen phosphorescence intensity collected at 1270 nm, following excitation at 355 nm of Luzitin-$Cl_2$Hep or phenalenone in air-saturated ethanol. The slope of the phosphorescence vs laser intensity dependence was employed to determine the singlet oxygen quantum yield of the sensitizer.

Figure 8:
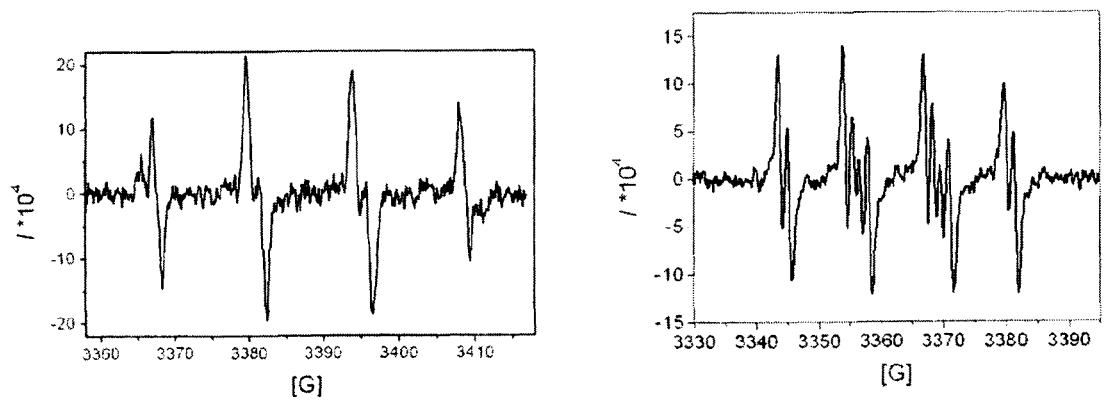

FIG. 8. EPR spectra obtained in the presence of 80 μM of Luzitin-Cl under irradiation. Left: with 40 mM BMPO in PBS the spectrum corresponds to that of the spin adduct of BMPO with the hydroxyl radical. Right: with 40 mM DMPO in DMSO the spectrum corresponds to that of the spin adduct of DMPO with the superoxide ion.

Figure 9:
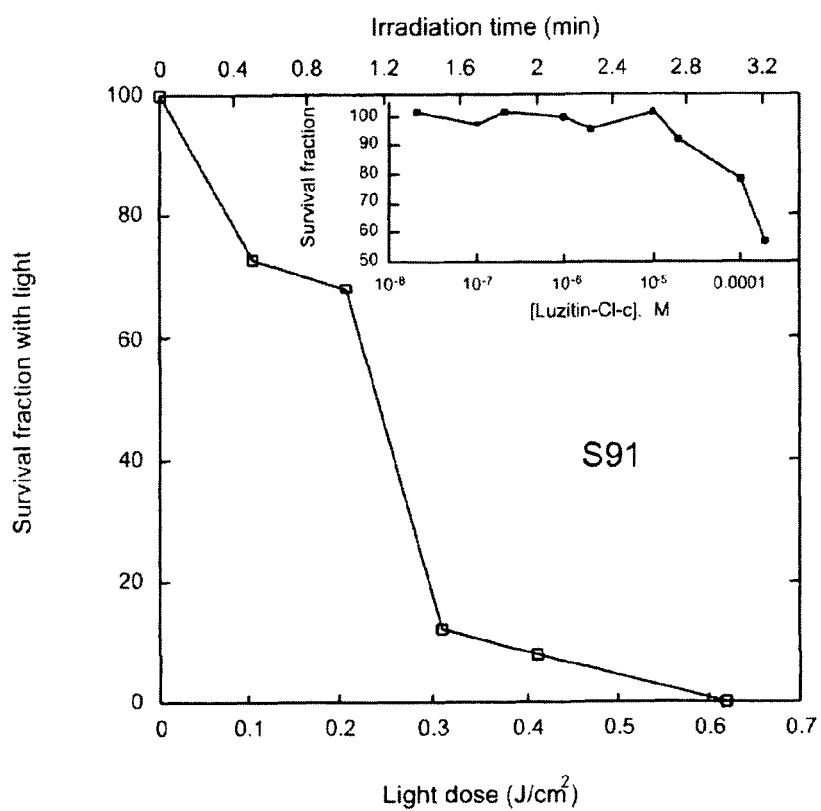

FIG. 9. Survival fraction of S91 cells (percentage) for various light doses in the presence of [Luzitin-Cl-c]=20 μM. The non-internalized photosensitizer was not removed before irradiation. Inset: Cytotoxicity in the dark of Luzitin-Cl-c towards S91 cells cell lines at different concentrations of sensitizer.

Figure 10:
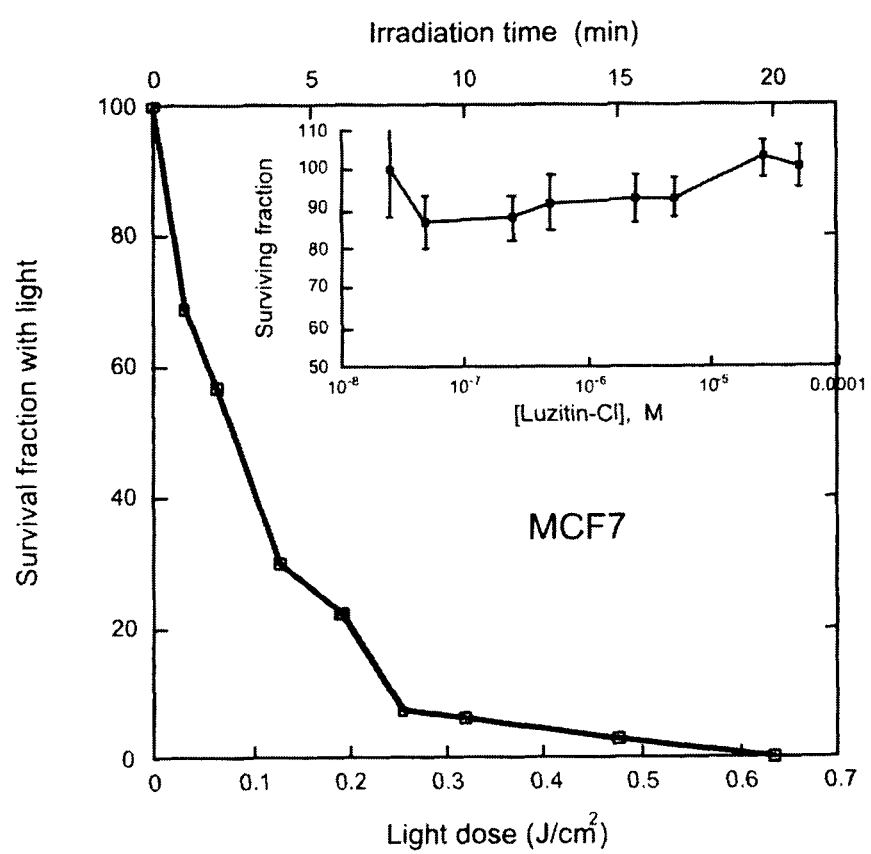

FIG. 10. Survival fraction of MCF7 cells (percentage) for various light doses in the presence of [Luzitin-Cl]=5 μM, after 12 h of incubation time. The non-internalized photosensitizer was removed before irradiation. Inset: cytotoxicity in the dark of Luzitin-Cl towards MCF cells cell lines at different concentrations of sensitizer. The effective light power is 0.53 mW/cm$^2$.

Figure 11:
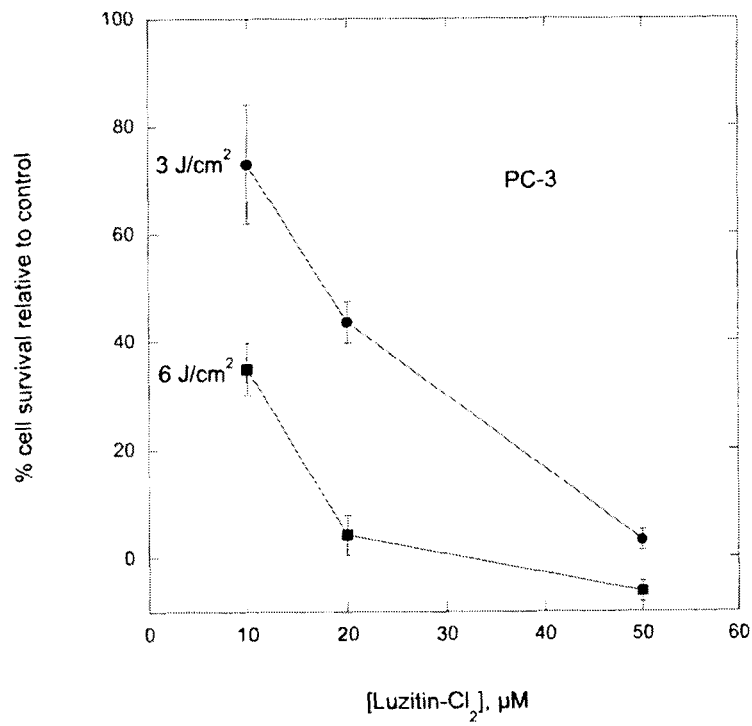

FIG. 11. Phototoxic effect of Luzitin-$Cl_2$ in prostate cancer cell line PC-3 after a drug-to-light interval of 24 hours. Cells in culture medium were irradiated with laser light of 748 nm for 30 or 60 seconds, which corresponds to light doses of 3 and 6 J/cm$^2$, respectively.

Figure 12:
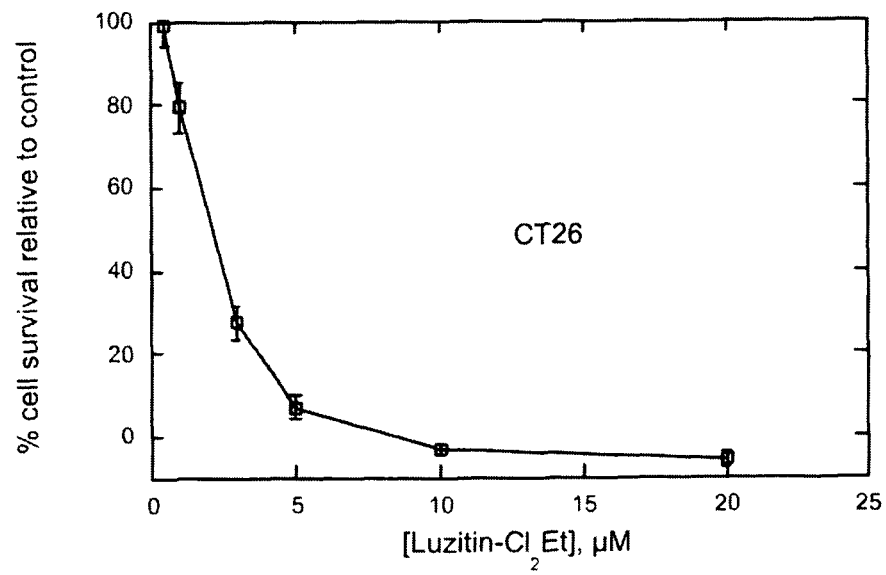

FIG. 12. Percentage of cell survival relative to control for various Luzitin-$Cl_2$Et concentrations in mouse colon carcinoma cell lines after a drug-to-light interval of 18 hours. The non-internalized photosensitizer was removed before irradiation. Cells in culture medium were irradiated with laser light of 748 nm for 60 seconds, which corresponds to light doses of 6 J/cm$^2$.

Figure 13:
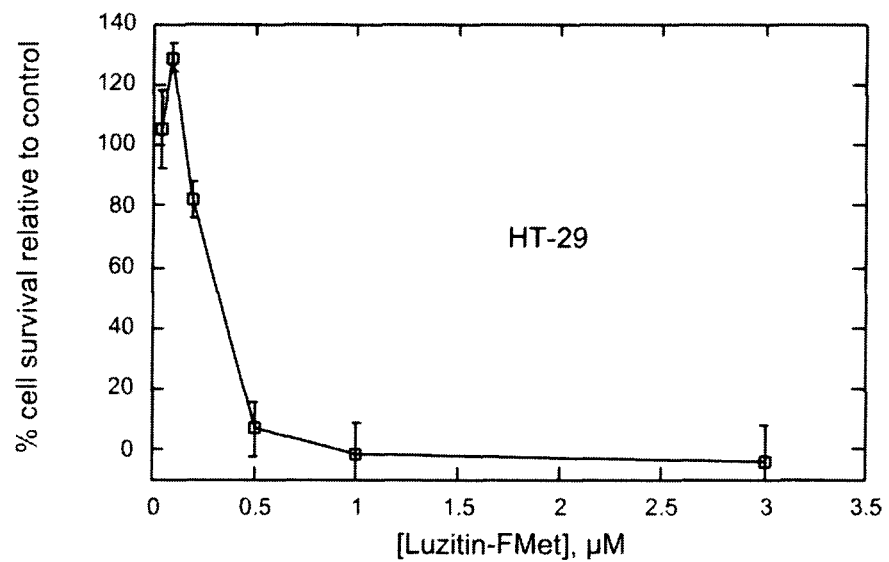

FIG. 13. Percentage of cell survival relative to control for various Luzitin-FMet concentrations in human adenocarcinoma cell lines after an incubation time of 18 hours. The non-internalized photosensitizer was removed before irradiation. Cells in culture medium were irradiated with laser light of 748 nm for 60 seconds, which corresponds to light doses of 6 J/cm$^2$.

Figure 14:
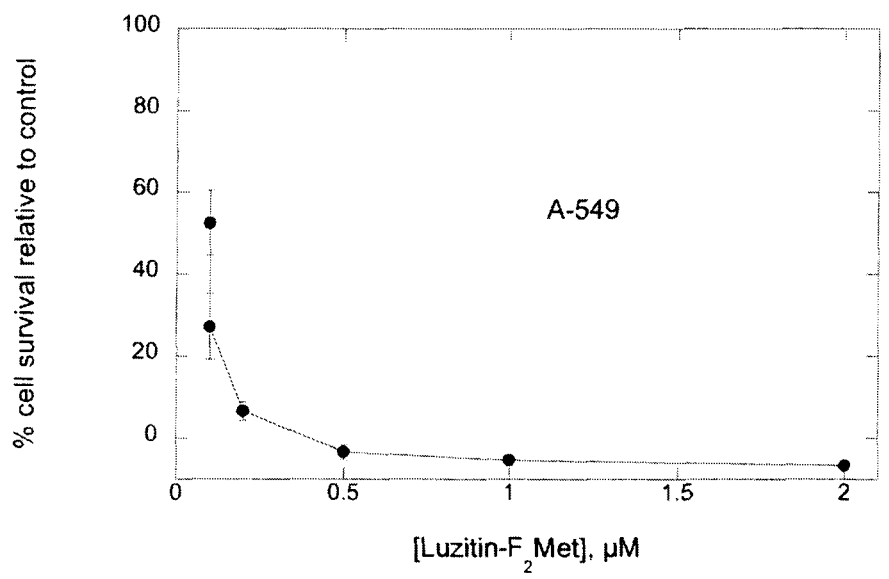

FIG. 14. Percentage of cell survival relative to control for various Luzitin-$F_2$Met concentrations in human non-small cell lung cancer lines after an incubation time of 18 hours. The non-internalized photosensitizer was removed before irradiation. Cells in culture medium were irradiated with laser light of 748 nm for 60 seconds, which corresponds to light doses of 6 J/cm$^2$.

Figure 15:
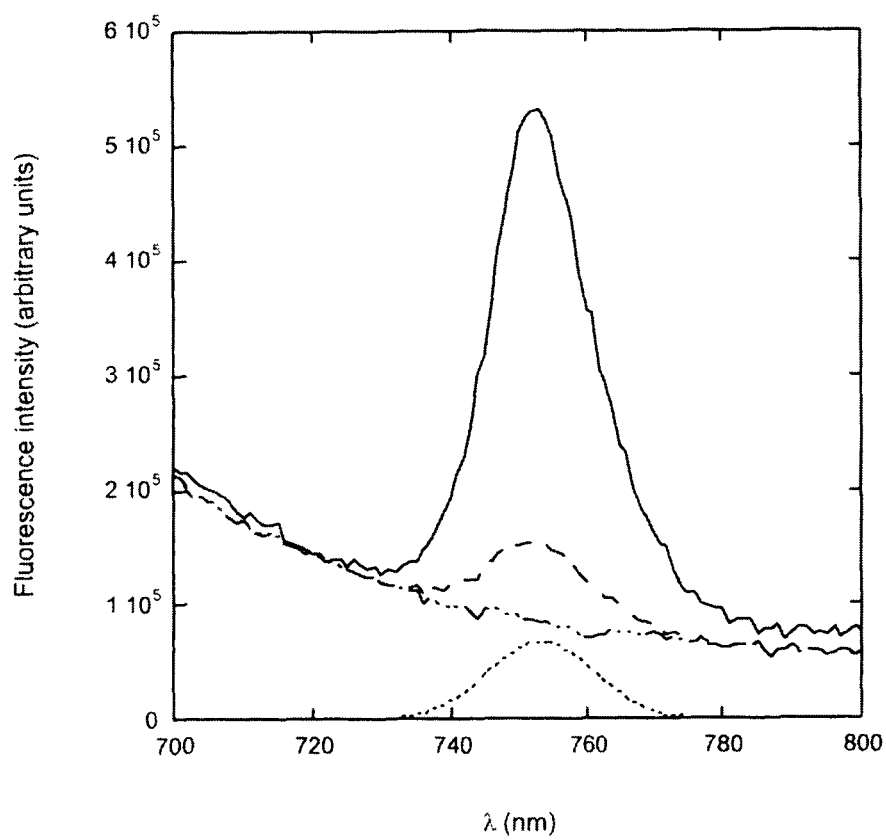

FIG. 15. Fluorescence of Luzitin-$Cl_2$Et at human serum concentrations of 3.26 nM (full line) and 0.26 nM (dashed line) used to determine its detection limit. Also shown is the base line (dash-dotted line) and Gaussian curve (dotted line) used to simulate the lowest concentration for a more precise determination of low intensity fluorescence.

Figure 16:
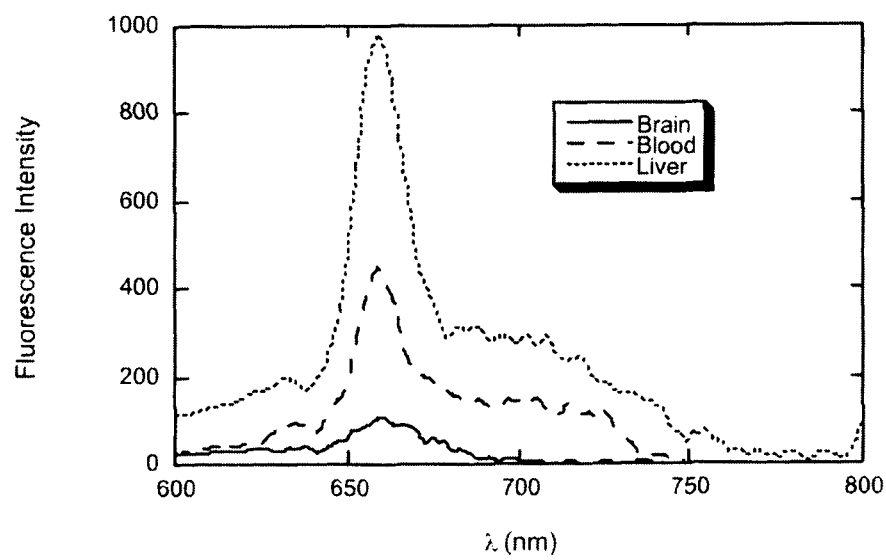

FIG. 16. Fluorescence of Luzitin-Cl-c divided by the mass of liver, blood and brain, respectively in order of intensity, following ip administration of 10 mg/kg in DBA/2 mice.

Figure 17:
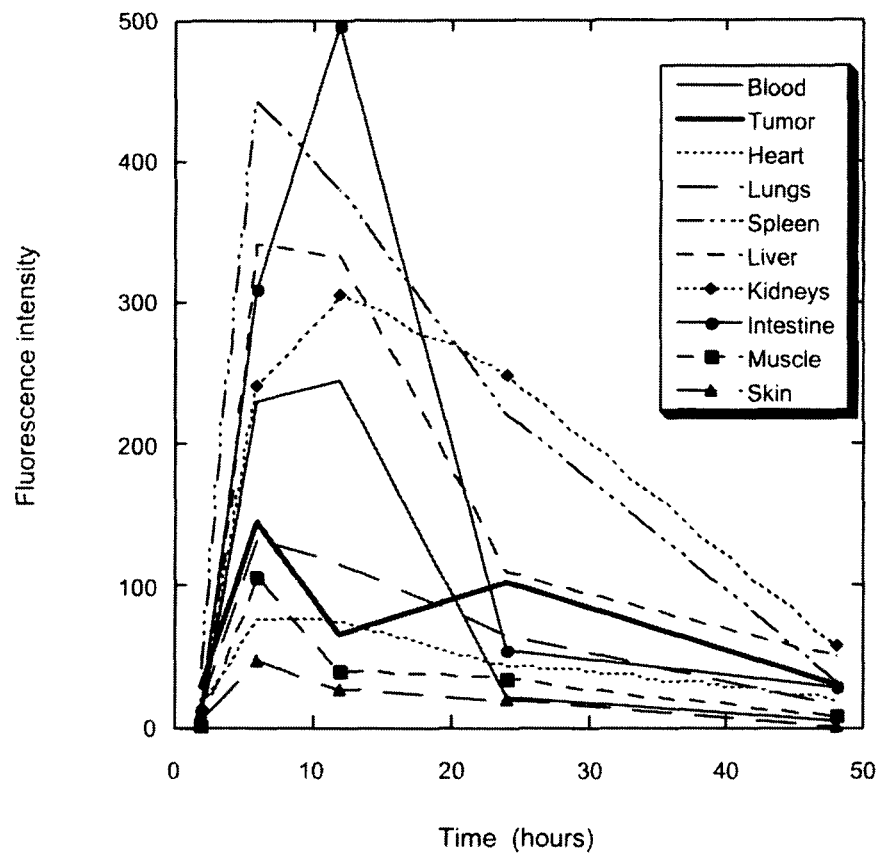

FIG. 17. Farmacokinetics and biodistribution of Luzitin-Cl following ip administration of 10 mg/kg in DBA/2 mice. The fluorescence intensity in the various tissues (blood, tumor, heart, lungs, spleen, liver, kidneys, intestine, muscle, skin) was normalized by their respective masses.

Figure 18:
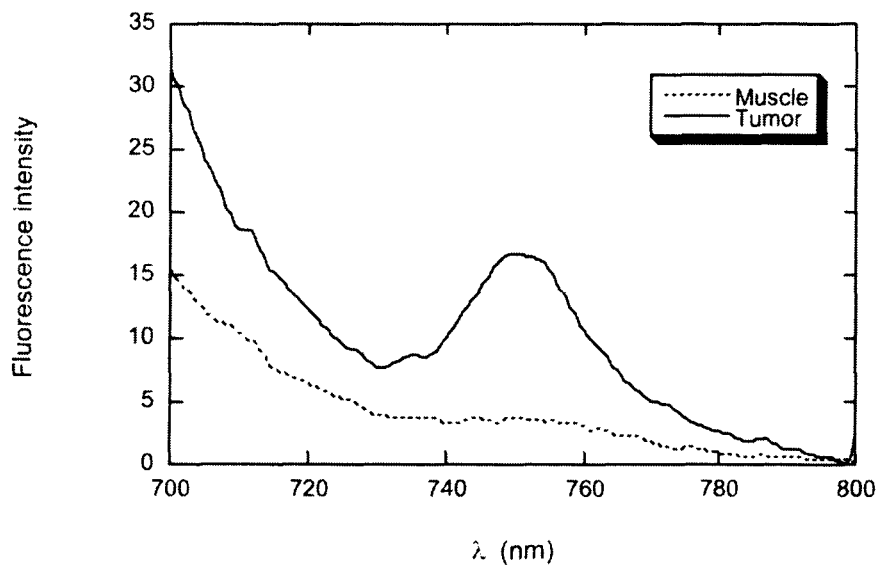

FIG. 18. Fluorescence of Luzitin-Cl$_2$Et divided by the mass of tumor and blood, respectively in order of intensity, following ip administration of 10 mg/kg in DBA/2 mice.

Figure 19:
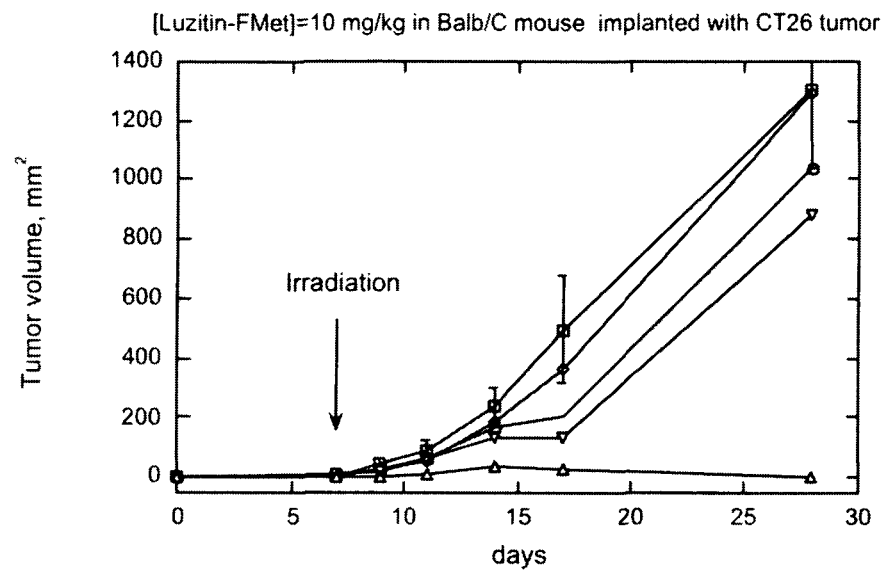

FIG. 19. Volume of the tumors in Balb/C mice with implanted CT26 tumors and treated with Luzitin-FMet. The thick line represents the average tumor sizes in four control animals, to which Luzitin-FMet was administered but not irradiated. The error bars are standard deviations. The thin lines represent individual animals treated with Luzitin-FMet and 132 J/cm$^2$ of laser light at 748 nm.

Figure 20:
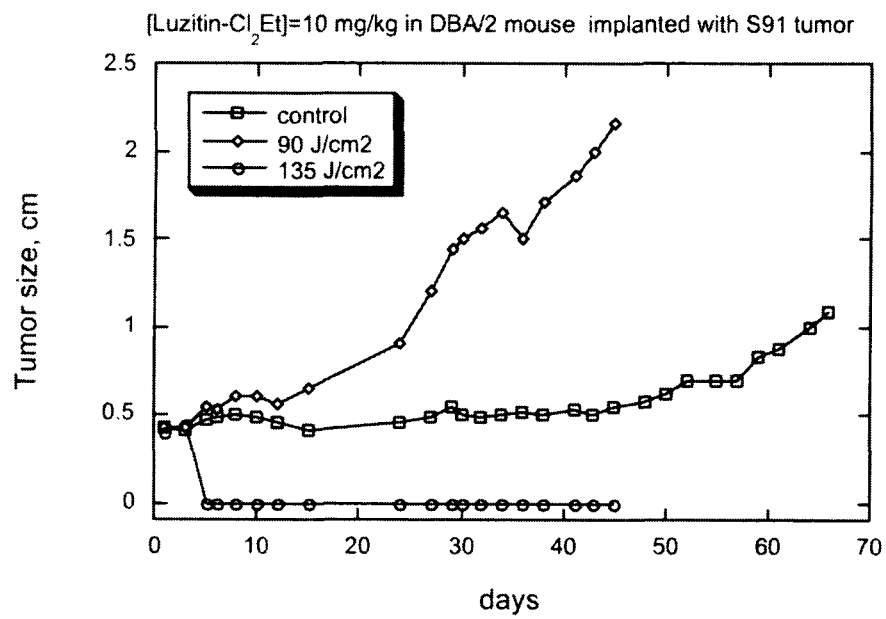

FIG. 20. Size of implanted S91 tumors in DBA/2 mice treated with Luzitin-Cl$_2$Et. Two laser light doses at 748 nm were employed.

Figure 21:
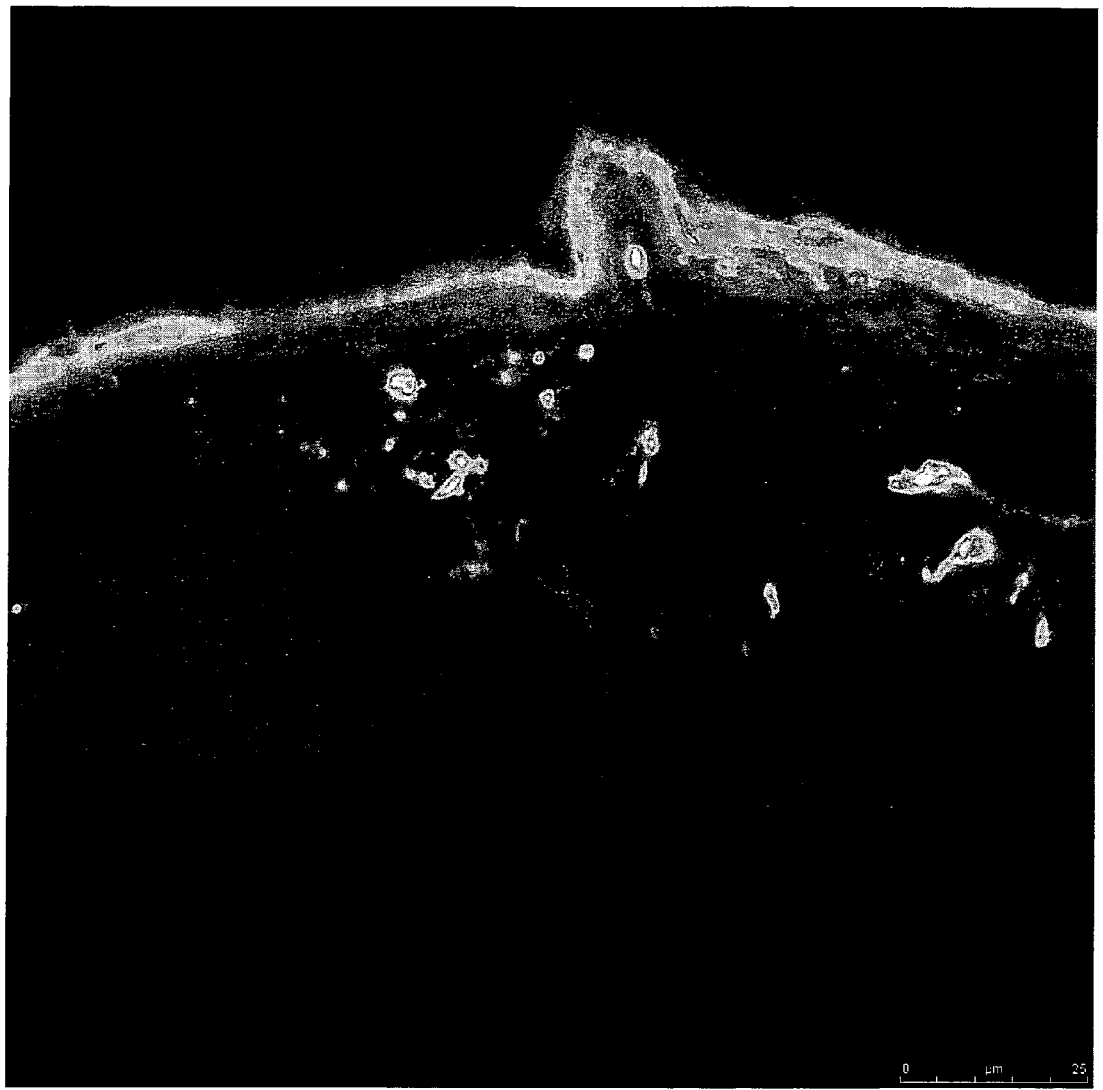

FIG. 21. Confocal fluorescence of Luzitin-FMet 3 h after topical application in the back of a minipig. Multiphoton excitation at 744 nm; full noise elimination; fluorescence plane images constructed by 6 pictures; 800 V @ detector; pinhole=379 µm. The photosensitizer diffused through 50 microns of stratum corneum and epidermis.

Figure 22:
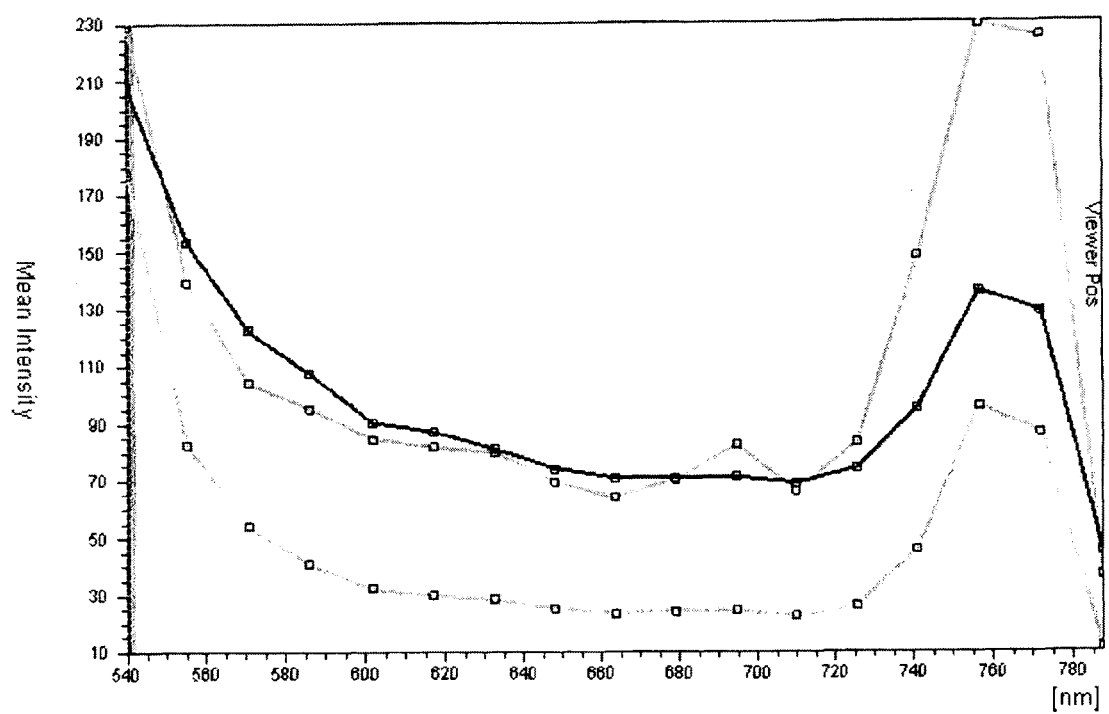

FIG. 22. Absorption spectra of Luzitin-FMet 3 h after topical application in the back of a minipig, obtained with confocal spectroscopy. The various lines correspond to measurements in different parts of the sample.

EXAMPLES

Example 1 Solid State Synthetic Procedure for Bacteriochlorins with Electron-Withdrawing Substituents This example illustrates the wide range of bacteriochlorins that can be synthesized by a procedure characterized by the absence of solvent and base, hence where only a porphyrin and a hydrazide (both in the solid state) are employed as starting materials.

In one preparation we mixed 60 mg ($6.8 \times 10^{-5}$ mol) of 5,10,15,20-tetrakis(2-trifluoromethylphenyl)porphyrin with 500 mg ($2.7 \times 10^{-3}$ mol) of p-toluenesulphonylhydrazide, both in very fine powders. They were added to a reactor, which was evacuated, sealed under N$_2$ and heated to a temperature higher than 100° C. for several minutes. After cooling (room temperature) the solid was removed and several portions of p-toluenesulphonylhydrazide 250 mg ($1.4 \times 10^{-3}$ mol) were added, until complete disappearance of the porphyrin Soret band. The bacteriochlorin was extracted with a small amount of organic solvent. The excess of hydrazide was removed by a short filtration on silica gel (column height 8 cm; column internal diameter 2.5 cm) using dichloromethane/n-hexane as elutant. After solvent evaporation and recrystallization from diethyl ether/pentane 90% of CF$_3$PhB was obtained with less than 5% of chlorin contamination.

The NMR of the isolated product is:

RMN $^1$H: (400.13 MHz, CDCl$_3$) δ, ppm: 7.47-7.45 (m, 4H); 7.26-7.20 (m, 8H); 7.15-7.12 (m, 4H); 2.42 (s, 4H); 2.37 (s, 4H); −1.27 (s, 2H).

Example 2. Solid State Synthetic Procedure for Halogenated Chlorins

In one preparation of 5,10,15,20-tetrakis(2-fluorophenyl-5-N-methylsulfamoylphenyl) chlorin, Luzitin-FMet-c, we mixed 50 mg ($4.72 \times 10^{-5}$ mol) of 5,10,15,20-tetrakis(2-fluorophenyl-5-N-methylsulfamoylphenyl)porphyrin with 18 mg ($9.44 \times 10^{-5}$ mol) of p-toluenesulphonylhydrazide. The reactor is evacuated, sealed under N$_2$ and is heated at a temperature higher than 100° C. for several minutes. After cooling (room temperature) the solid was removed with a small amount of organic solvent, and the excess of hydrazide was removed by a short filtration on silica gel using ethylacetate/hexane as elutant. A mixture of chlorin contaminated with approximately 10% of bacteriochlorin was obtained. The mixture of chlorin and bacteriochlorin was dissolved in dichloromethane and oxidized to the corresponding chlorin by heating at 50° C. in the presence of air.

After recrystallization from diethyl ether/pentane 90% of Luzitin-FMet-c was obtained with less than 1% of bacteriochlorin contamination. FIG. 2 shows the absorption spectrum of the final product.

Example 3. Solid State Synthetic Procedure for Halogenated Bacteriochlorins

This example describes a clean, simple, economical and environmentally-benign synthetic method, involving a solvent-free one-pot synthesis of halogenated amphiphilic bacteriochlorins.

The appropriate porphyrin (solid) and the p-toluenesulphonylhydrazide (solid) are ground into very fine powders and thoroughly mixed. Next they are introduced into a reactor and evacuated to high vacuum. The reactor is then sealed and kept under vacuum, or repeatedly washed with an inert gas. Finally, the reactor is heated (70-200° C.) during 1-340 min, while sealed. Once the reaction is completed and the reactor brought to room temperature, the corresponding bacteriochlorin is obtained with 90% yield. After a short filtration by silica gel column, a bacteriochlorin with a contamination of less than 5% of the corresponding chlorin is obtained.

In one preparation of 5,10,15,20-tetrakis(2,6-dichloro-3-N-ethylsulfamoylphenyl)bacteriochlorin, Luzitin-Cl$_2$Et, with this method we mixed 50 mg ($3.8 \times 10^{-5}$ mol) of 5,10,15,20-tetrakis(2,6-dichloro-3-sulphoethylphenyl)porphyrin with 188 mg ($10^{-3}$ mol) of p-toluenesulphonylhydrazide, evacuated the reactor with an Edwards pump, sealed and then heated the reactor to more than 70° C. for several minutes. After cooling (room temperature), the solid is removed with a small amount of diethyl ether and the excess of hydrazide is removed by a short filtration on silica gel (column height 4 cm; column internal diameter 2.5 cm) using ethyl acetate/diethyl ether, as elutant. After solvent evaporation the resulting solid is recrystallized from diethyl ether/pentane to give Luzitin-Cl2Et with 90% yield. The absorption spectrum in FIG. 3 reveals the presence of less than 5% of the corresponding chlorin. The molar absorption coefficient of this and other bacteriochlorins is presented in Table 1, corrected for the amount of chlorin sometimes present in the samples. The comparison between the spectra of FIG. 3 below and that of FIG. 2 in the patent PCT/EP2005/012212, also of the University of Coimbra, reveals that the chlorin impurity is reduced by at least a factor of 10 by this new synthetic procedure, which is also is more economical, less laborious and environmentally benign. The NMR and MS of the isolated product are as follows:

RMN $^1$H: (300 MHz, CDCl$_3$) δ, ppm: 8.42 (d, J=8.55 Hz, 4H, p-H); 7.88 (d, J=8.55 Hz, 4H, m-H); 7.84-7.82 (m, 4H, β-H); 5.01 (m, 4H, N—H); 3.91 (s, 8H, β-H); 3.22 (m, 8H, CH$_2$); 1.24 (t, 12H, J=6.73 Hz, CH$_3$); −1.29 (s, 2H, NH).

MS: (MALDI-TOF), m/z: 1322.0 [M]$^+$.

Example 4. Atropisomers in Halogenated Bacteriochlorins

This example shows that stable atropisomers exist in halogenated and sulfonated bacteriochlorins and that they can be easily separated. It also shows that the more polar atropisomers have higher extinction coefficient in the infrared.

Using the procedure described in Example 3 but using a larger column (column height 8 cm; column internal diameter 2.5 cm) with ethyl acetate/n-hexane (1:1) as first elutant and ethyl acetate/n-hexane (3:1) as last elutant, we observed a separation of 5,10,15,20-tetrakis(2,6-dichloro-3-N-ethyl-sulfamoylphenyl)bacteriochlorin, Luzitin-Cl$_2$Et, in two fractions. Each fraction showed two spots in TLC, that were identified as a mixture of the less polar atropisomers $\alpha\beta\alpha\beta+\alpha_2\beta_2$ or of more polar ones $\beta\alpha_3+\alpha_4$. FIG. 4 shows the absorption spectrum of the mixture of the atropisomers with higher polarity. This fraction exhibits a 50% enhancement of the c at 750 nm band, that reaches 150,000 M$^{-1}$ cm$^{-1}$.

Example 5. pH Stability of Halogenated and Sulfonated Bacteriochlorins

This example demonstrates the stability of halogenated and sulfonated bacteriochlorins at pH 1 and 37° C., that is, in the acidity found in the stomach.

Luzitin-Cl$_2$ was dissolved in neutral aqueous solution and equilibrated to 37° C. to give the absorption spectrum represented in FIG. 5. HCl in aqueous solution was added drop wise, to lower the pH to 1 and 2 hours later the absorption spectrum of Luzitin-Cl2 at pH 1 was registered. Then, an aqueous solution of NaOH was added to neutralize the solution and a new absorption spectrum was registered 3 hours later. FIG. 5 shows the absorption spectra corrected for the dilution produced by the addition of HCl and NaOH in aqueous solution. The spectral changes observed at low pH are due to the protonation of the pyrrole ring, but are reversed when the acidity is neutralized. Under these conditions, nearly half of Luzitin-Cl$_2$ is recovered and the other half in transformed into the corresponding chlorin.

Example 6. Light Stability of Halogenated and Sulfonated Bacteriochlorins

This example demonstrates the increased stability of halogenated and sulfonated bacteriochlorins towards irradiation by infrared light, that resolves problems of lability found in other bacteriochlorins, either of synthetic origin, such as 5,10,15,20-tetrakis(3-hydroxyphenyl)bacteriochlorin, or derived from natural products, such as Tookad®.

Luzitin-FMet was dissolved in PBS:methanol (2:3), transferred to a 1 cm quartz cell and its absorption spectrum was registered, FIG. 6. The quartz cell was then placed in the beam of the 748 nm Lynx diode laser, previously unfocused to have a beam diameter coincident with the window of the quartz cell. The laser power measured under these conditions was 28.8 mW. Every 5 minutes the irradiation was interrupted and a new absorption spectrum was registered. This procedure was followed for 65 minutes. The photobleaching follows the kinetics of a first-order reaction in the time window of the experiment. FIG. 6 also shows the absorption spectrum after the irradiation. Whereas the bacteriochlorin peak at 743 nm is reduced from an absorbance of 1.128 to 0.337, the absorption of the chlorin only increases from 0.114 to 0.151. Taking into consideration the molar absorption coefficients of the compounds at these wavelengths, it is clear that whereas 70% of the bacteriochlorin is destroyed during the irradiation, only a few percent of chlorin are formed. The remaining products, do not have well-resolved spectra in the visible/IR, and the dominant photodegradation process can be described as photobleaching.

The half-live of the photobleaching was measured for different laser intensities and it was shown to be proportional to the laser power. The half-lives of other bacteriochlorins normalized 100 mW laser irradiation at 748 nm are presented in Table 1, together with the literature data for the photodegradation of Foscan® and Tookad® normalized for the same light intensity. It was also observed that the half-live to Luzitin-Cl is increased by a factor of 30 when the PBS solution of the photosensitizer is saturated with Argon, which reduces the oxygen concentration in the solution. This shows the participation of ROS in the photobleaching.

Example 7. Efficient Photogeneration of Singlet Oxygen

This example describes the efficiency generation of singlet oxygen in the presence of Luzitins, light of an appropriate wavelength and molecular oxygen dissolved in solution.

An air-saturated solution of Luzitin-Cl$_2$Hep in ethanol with an absorbance ca. 0.2 at 355 nm was excited in a 1 cm quartz cuvette by a pulsed Nd:YAG laser, and the singlet oxygen emission was followed at 1270 nm, using the equipment and methods previously described. The intensity of the singlet oxygen phosphorescence was studied as a function of the laser intensity. A similar study was made with phenalenone in ethanol, at a concentration matching the absorbance of Luzitin-Cl$_2$Hep at 355 nm. FIG. 7 shows the laser energy dependence of the singlet oxygen phosphorescence intensity measured at 1270 nm after Luzitin-Cl$_2$Hep or phenalenone excitation at 355 nm in air-saturated ethanol. Various laser energies were employed and from the slopes of the energy dependence of singlet oxygen emission and the value of $\Phi_\Delta=0.95$ for phenalenone in this ethanol, we obtained $\Phi_\Delta=0.78$ for Luzitin-Cl$_2$Hep. Values for other bacteriochlorins are presented in Table 1.

The photostability of these bacteriochlorins associated with their ca. 70% quantum efficiency of singlet oxygen production, implies that one given molecule of bacteriochlorin under continuous irradiation will produce locally a very large amount of electronically excited oxygen molecules before it photobleaches. Some 30% of the energy absorbed by the sensitizer is lost to other processes, some of them identified in the following example.

Example 8. Photogeneration of Reactive Oxygen Species (ROS)

This example describes the generation of reactive oxygen species, namely the superoxide ion and the hydroxyl radical using Luzitin-Cl as sensitizer.

In order to assess the photogeneration of superoxide ion and the hydroxyl radical by Luzitin-Cl, EPR spectra in the presence of 30-80 µM of Luzitin-Cl and 40 mM BMPO were measured in the following conditions:
a) Air-saturated aqueous solution in the dark.
b) Nitrogen-saturated aqueous solution irradiated with the Hamamatsu diode laser for 8 minutes.
c) Air-saturated aqueous solution irradiated with the Hamamatsu diode laser for 4 minutes.
d) Air-saturated aqueous solution irradiated with the Hamamatsu diode laser for 8 minutes.
e) Air-saturated aqueous solution irradiated with the Hamamatsu diode laser for 16 minutes.

f) Air-saturated aqueous solution irradiated with the Hamamatsu diode laser for 16 minutes, in the presence of superoxide dismutase (50 μg/ml).

g) Air-saturated aqueous solution irradiated with the Hamamatsu diode laser for 16 minutes, in the presence of catalase (30 μg/ml).

Under experimental conditions (a) and (b) no ROS-BMPO adduct was detected. However, experimental conditions (c), (d) and (e) lead to the detection of a BMPO adduct which is that formed between BMPO and the hydroxyl radical, FIG. 8. The presence of light is necessary to form such adduct. Experimental condition (f) gives no signal, with means that superoxide dismutase, a known scavenger of superoxide ion, inhibits the formation of the BMPO-hydroxyl radical adduct. Additionally, experimental condition (g) also gives no signal, and proves that catalase, which breaks down hydrogen peroxide into water and molecular oxygen, also inhibits the formation of the BMPO-hydroxyl radical adduct. These results indicate that hydroxyl radicals are not formed directly from the photosensitizer and molecular oxygen but rather as a secondary product. The inhibition observed by superoxide dismutase is compelling evidence for the formation of superoxide ion. The inhibition observed by catalase suggests that hydrogen peroxide is also a precursor of the hydroxyl radical.

Similar experiments were conducted with DMPO in DMSO. We detected the DMPO-superoxide adduct in the presence of air and light, FIG. 8. However, in the absence of air or light, or in the presence of superoxide dismutase, this adduct was not observed.

Taken together, these data indicate the formation of superoxide ion, followed the formation of hydrogen peroxide and, subsequently, of the hydroxyl radical, all of them are very well documented reactive oxygen species capable of producing damage to cells. These ROS complement the ca. 70% singlet oxygen formation efficiency of these bacteriochlorins and shows that remaining 30% of the energy absorbed by the sensitizer are not lost, but rather employed in the formation of other cytotoxic species, in addition to singlet oxygen.

Example 9. In Vitro Phototoxicity of Luzitin-Cl-c Towards Mouse Melanoma Cell Lines Under Standard Lamp Irradiation This example shows that Luzitins are very toxic to mouse melanoma cells under filtered halogen light irradiation, at concentrations where their dark toxicity is negligible.

The cytotoxicity in the dark and the photosensitizing activity of Luzitin-Cl-c in S91 (mouse melanoma) cell lines were measured with the materials and methods described before, except that after incubation cells were not washed to remove the non-internalized photosensitizer before irradiation. The inset in FIG. 9 shows the cytotoxicity in the dark of different concentrations of Luzitin-Cl-c for an incubation time of 120 minutes. FIG. 9 shows the survival fraction of S91 cells for different light doses, when the cells are irradiated in the presence of [Luzitin-Cl-c]=20 μM. Light doses required to kill 90% ($LD_{90}$) or 50% ($LD_{50}$) of the cells in the culture are presented in Table 3.

Example 10. In Vitro Phototoxicity of Luzitin-Cl Towards Mouse Melanoma Cell Lines Under Standard Lamp Irradiation This example shows that Luzitins are very toxic to human breast carcinoma cells under filtered halogen light irradiation, at concentrations where their dark toxicity is negligible.

The cytotoxicity in the dark and the photosensitizing activity of Luzitin-Cl in MCF7 (human breast carcinoma) cell lines were measured with the materials and methods described before. The inset in FIG. 10 shows the cytotoxicity in the dark of different concentrations of Luzitin-Cl and an incubation time of 12 hours. FIG. 10 shows the survival fraction of MCF7 cells for [Luzitin-Cl]=5 μM and various light doses. Clearly, a 5 μM concentration of Luzitin-Cl produced 100% cell kill on exposing to filtered halogen light at a dose of 0.6 $J/cm^2$. Light doses required to kill 90% ($LD_{90}$) or 50% ($LD_{50}$) of the cells in the culture are presented in Table 4.

Example 11. In Vitro Phototoxicity of Luzitin-$Cl_2$ Towards Human Prostate Carcinoma Under Laser Irradiation This example shows that Luzitins are very toxic to human prostate carcinoma cells under laser irradiation, at concentrations where their dark toxicity is negligible.

The cytotoxicity in the dark of Luzitin-$Cl_2$ in PC-3 (human prostate carcinoma) cell lines were measured with the materials and methods described before. According to these experiments, 0.05 mM is the highest concentration of Luzitin-$Cl_2$ that causes relatively no effect in the viability of the cell lines in test in the dark. This will be the reference concentration in the following phototoxicity studies.

The photosensitizing activity of Luzitin-$Cl_2$ in PC-3 cell lines were measured with the materials and methods described before. Survival fraction for light doses of 3 and 6 $J/cm^2$ and an incubation time of 24 hours is depicted in FIG. 11 for various concentrations of this photosensitizer. According to FIG. 11, [Luzitin-$Cl_2$]=20 μM produces 100% cell kill on exposing to a laser light dose of 6 $J/cm^2$.

Example 12. In Vitro Phototoxicity of Luzitin-$Cl_2$Et Towards Mouse Colon Carcinoma Cell Lines Under Laser Irradiation This example shows that Luzitins are very toxic to mouse colon carcinoma cells under laser irradiation, at concentrations where their dark toxicity is negligible.

The cytotoxicity in the dark of Luzitin-$Cl_2$Et in CT26 (mouse colon carcinoma) cell lines could not be measured in terms of $IC_{50}$ because the compound precipitates in the culture medium before attaining this level of cytotoxicity. A concentration of 50 μM is the highest concentration of Luzitin-$Cl_2$Et that causes relatively no effect in the viability of these cell lines in the dark.

The photosensitizing activity of Luzitin-$Cl_2$Et in CT26 cell lines were measured with the materials and methods described before. Survival fraction for light doses of 6 $J/cm^2$ and an incubation time of 18 hours is depicted in FIG. 12 for various concentrations of this photosensitizer. This Figure shows that Luzitin-$Cl_2$Et at a concentration of 5 μM produced 90% cells kill on exposing to laser light dose of 6 $J/cm^2$, $LD_{90}$=5 μM. According to FIG. 12, [Luzitin-$Cl_2$]=10 μM produces 100% cell kill on exposing to a laser light dose of 6 $J/cm^2$. Table 6 presents the Luzitin-$Cl_2$Et concentrations required to attain $LD_{90}$ in various other cell lines under 6 $J/cm^2$ diode laser irradiation at 28.5 mW.

Example 13. In Vitro Phototoxicity of Luzitin-FMet Towards Human Colon Carcinoma Cell Under Laser Irradiation This example shows that Luzitins are very toxic to human colon carcinoma cells under laser irradiation, at concentrations where their dark toxicity is negligible.

The cytotoxicity in the dark of Luzitin-FMet in HT-29 (human colon adenocarcinoma) cell lines could not be measured in terms of $IC_{50}$ because the compound precipitates in the culture medium before attaining this level of cytotoxicity. A concentration of 50 μM is the highest concentration of Luzitin-FMet that causes relatively no effect in the viability of the cell lines in test in the dark.

The photosensitizing activity of Luzitin-FMet in HT-29 cell lines were measured with the materials and methods described before. Survival fraction for light doses of 6 J/cm$^2$ and an incubation time of 18 hours is depicted in FIG. 13 for various concentrations of this photosensitizer. This Figure shows that Luzitin-FMet at a concentration of 0.5 μM produced 90% cells kill on exposing to laser light dose of 6 J/cm$^2$, $LD_{90}$=1 μM. According to FIG. 13, [Luzitin-FMet]=1 μM produces 100% cell kill on exposing to a laser light dose of 6 J/cm$^2$. Table 6 presents the Luzitin-FMet concentrations required to attain $LD_{90}$ in various other cell lines under 6 J/cm$^2$ diode laser irradiation at 28.5 mW.

Example 14. In Vitro Phototoxicity of Luzitin-F$_2$Met Towards Human Non-Small Cell Lung Carcinoma Under Laser Irradiation This example shows that Luzitins are very toxic to human non-small cell lung cancer cells under laser irradiation, at concentrations where their dark toxicity is negligible.

The cytotoxicity in the dark of Luzitin-F$_2$Met in A-549 (human non-small cell lung cancer) cell lines could not be measured in terms of $IC_{50}$ because the compound precipitates in the culture medium before attaining this level of cytotoxicity. A concentration of 50 mM is the highest concentration of Luzitin-F$_2$Met that causes relatively no effect in the viability of the cell lines in test in the dark.

Survival fraction for light doses of 6 J/cm$^2$ and an incubation time of 18 hours is depicted in FIG. 14 for various concentrations of this photosensitizer. This Figure shows that Luzitin-F$_2$Met at a concentration of 0.5 μM produced 90% cells kill on exposing to laser light dose of 6 J/cm$^2$, $LD_{90}$=0.5 μM. According to FIG. 14. [Luzitin-F$_2$Met]=0.5 μM produces 100% cell kill on exposing to a laser light dose of 6 J/cm$^2$. Table 6 presents the Luzitin-F$_2$Met concentrations required to attain $LD_{90}$ in various other cell lines under 6 J/cm$^2$ diode laser irradiation at 28.5 mW.

Example 15. Fluorescence Detection Limit

This example shows the extreme sensitivity and selectivity of detection of Luzitins in biological samples.

Solutions of different concentrations where prepared by dilution to in human serum of a 1% stock solution of Luzitin-Cl$_2$Et in ethanol. The concentrations ranged from 0.2 nM to 10 nM. The samples were excited at 514 nm in the spectrofluorimeter described above, using slits 4:5:3: for excitation and emission. The emission was collected in the infrared as illustrated in FIG. 15.

The detection limit was determined using the equation $$L.D. = \frac{[3.3 \cdot S_{y/x}]}{b}$$

where $S_{y/x}$ is the standard deviation of the calibration curve and b is its slope. The detection limit of 0.17 nM (or 0.2 ng/g) was obtained.

Example 16. In Vivo Toxicity in the Dark

This example shows that Luzitins are not toxic to mice at concentrations much higher that those approved for PDT with commercially available photosensitizers.

The mice were divided into the following experimental groups:
a) 10 animals received 2 mg/kg of Luzitin-Cl
b) 10 animals received 5 mg/kg Luzitin-Cl
c) 10 animals received 10 mg/kg Luzitin-Cl
d) 10 animals received 15 mg/kg Luzitin-Cl
e) 10 animals received 20 mg/kg Luzitin-Cl
f) 10 animals received no treatment, and are the control group.

The solutions of Luzitin-Cl (0.5 ml) were injected subcutaneously and for 30 days the animals were closely observed. In first 6 days after injection the animals from the group (e) revealed sensitivity to the light and some of the group (d) also revealed a slight sensitivity. They manifested such sensitivity by moving away from light sources directly pointed at them. The animals were weighted regularly but no significant mass changes were observed for any of them. After 30 days the animals were anaesthetized using Morbital (Biowet, Poland), their organs and tissue samples were excised, and blood morphology as well as histology of selected organs tests was performed. No changes were observed in the blood or in organs.

The doses employed in these dark toxicity assays were 10 times higher than those recommended for the use of Photofrin® and 100 timer higher than the doses employed with Foscan®. And yet, the threshold for measurable dark toxicity in mice was not attained. This provides evidence that higher doses of Luzitins can be employed in PDT than of Photofrin® or Foscan®.

Example 17. Chlorin Biodistribution Following Ip Administration

This example shows that Luzitins can cross the blood-brain barrier two hours after ip administration.

Luzitin-Cl-c was administered at a dose of 10 mg/kg to DBA/2 mice via intraperitoneal injection. Chlorin distribution in the tissues was analyzed 2 h after administration. The animals were anaesthetized using Morbital (Biowet, Poland), and some of their organs, including the brain, were excised, weighted and then stored at −30° C. until further analysis. The content of pigments in the tissue samples was analyzed spectrofluorometrically. In order to extract the pigments, tissue samples were homogenized 1 min in 7 ml of ice-cold 90% aqueous acetone, using a tissue homogenizer MPW-120 (Medical Instruments, Poland) at the speed of 10 000 rpm. The homogenate was centrifuged at 2000 g for 10 min at 4° C., the supernatant was collected and the pellet was re-extracted with 90% aqueous acetone to ensure a complete recovery of the pigment. The extracts were pooled and analyzed for pigment content. The samples were excited at 413 nm and the fluorescence spectra were recorded in the range between 600 and 800 nm. FIG. 16 illustrates the fluorescence intensity from the brain, blood and liver, normalized by their respective masses.

The blood-brain distribution of the sensitizer was 4:1 two hours after ip administration in DBA/2 mice. This is the proof-of-principle that suitable Luzitins can cross the blood-brain barrier in significant amounts to become an active photosensitizer in the brain. It is shown in the subsequent example that this class of sensitizers tends to accumulate in tumors, further increasing the amount of photosensitizer that will be available for the treatment of brain tumors.

Example 18. Bacteriochlorin Farmacokinetics Following Ip Administration

This example shows that after ip administration Luzitins first accumulate in tumors, and then are cleared at slower rates.

The tumor model was S91 Cloudman melanoma cells, cultured as monolayer in the RPMI medium, containing 5% fetal calf serum and supplemented with antibiotics. The cells were grown at 37° C. in humidified atmosphere containing 5% $CO_2$. The melanoma cells (~1×10$^6$) were taken up in 0.1 ml phosphate buffered saline (PBS) and implanted subcutaneously to the right flank of the animal. The tumors grew visible in ten days after the implantation. The animals were treated three weeks after the injection.

Luzitin-Cl was administered at a dose of 10 mg/kg to DBA/2 mice via intraperitoneal injection. Bacteriochlorin tissue distributions were analyzed at following intervals: 2 h, 6 h, 12 h, 24 h and 48 h after intraperitoneal administration. The animals were anaesthetized with ketamine and xylazine, their organs and tissue samples were excised, weighted and then stored at −30° C. until further analysis. The content of pigments in the tissue samples was analyzed spectrofluorometrically. In order to extract the pigments, tissue samples were homogenized 1 min in 7 ml of ice-cold solution ethanol/DMSO (75:25), using a tissue homogenizer MPW-120 (Medical Instruments, Poland) at the speed of 10 000 rpm. The homogenate was centrifuged at 2000 g for 10 min at 4° C., the supernatant was collected and the pellet was re-extracted with the ethanol:DMSO solution to ensure a complete recovery of the pigment. The extracts were pooled and analyzed for pigment content. The samples were excited at 517 nm and the fluorescence spectra were recorded in the range between 600 and 850 nm. FIG. 17 illustrates the fluorescence intensity from the tumor and several organs, normalized by their respective masses.

There is a significant accumulation of this photosensitizer in the tumor one day after the intraperitoneal administration, when it reaches a concentration 3 times higher than in muscle. Additionally, the accumulation in the skin is negligible, which explains the lack of photosensitivity of the mice in the dark toxicity studies. Finally, the photosensitizer was cleared from most of the organs in 24 h. These farmacokinetics are very favorable for the selection of a time-window for PDT treatment where side effects are reduced and the efficiency of the treatment is maximized.

Similar studies were performed with other Luzitins, and Luzitin-Cl$_2$Et showed a very strong tumor vs muscle selectivity, FIG. 18.

Example 19. PDT of Mouse Colon Carcinoma in Balb/C Mice Using Luzitin-FMet

This example shows that Luzitins when exposed to light of an appropriate wavelength produce tumor regression/necrosis.

The tumor model was CT26 mouse colon carcinoma, cultured as monolayer in the RPMI medium, containing 5% fetal calf serum and supplemented with antibiotics. The cells were grown at 37° C. in humidified atmosphere containing 5% $CO_2$. The carcinoma cells (~1×10$^6$) were taken up in 0.1 ml phosphate buffered saline (PBS) and implanted subcutaneously to the right flank of the Balb/C mice. The tumors grew to reach 5 mm in diameter in about one week after the implantation. No spontaneous necrosis was observed. The treatment was initiated when the tumor attained 5 mm in diameter in each animal. The day the tumors reached the treatment size, the mice were injected via i.p. with a dose of 10 mg/kg of Luzitin-FMet in PEG400. At 24 h post-injection, four mice were anesthetized with ketamine and xylazine, and treated with the Hamamatsu 748 nm diode laser described before, at a fluence rate of 100 mW/cm$^2$ for 22 minutes (total fluence of 132 J/cm$^2$). Four other mice were not treated and served as control. The mice were checked daily, the tumors were measured using two orthogonal measurements L and W (perpendicular to L) and the volumes were calculated using the formula V=L×W$^2$/2 and recorded.

FIG. 19 shows the relative tumor volume measured at different days after laser irradiation. The size of the tumors in the animals treated are smaller than the average size of the control animals and in one case the tumor completely disappeared.

Example 20. PDT of Melanoma Cells in DBA/2 Mice Using Luzitin-Cl$_2$Et

This example shows that Luzitins when exposed to light of an appropriate wavelength produce tumor regression/necrosis.

The tumor model were S91 Cloudman melanoma cells, cultured as monolayer in the RPMI medium, containing 5% fetal calf serum and supplemented with antibiotics. The cells were grown at 37° C. in humidified atmosphere containing 5% $CO_2$. The melanoma cells (~1×10$^6$) were taken up in 0.1 ml phosphate buffered saline (PBS) and implanted subcutaneously to the right flank of the DBA/2 mice. The tumors grew to reach 5 mm in about one week after the implantation. No spontaneous necrosis was observed. The treatment was initiated when the tumor attained 5 mm in diameter in each animal. The day the tumors reached the treatment size, the mice were injected via i.p. with a dose of 10 mg/kg of Luzitin-C12Et in PEG400. At 24 h post-injection, the mice were anesthetized with ketamine and xylazine, and restrained in plastic holders, then treated with different light doses with the Hamamatsu 748 nm diode laser described before. Within minutes of the irradiation, the tumor area presented evident signals of necroses, that extended to all the irradiated area within a few hours. The mice were checked daily, and the size of the tumors was measured and recorded. FIG. 20 shows the tumor size measured at different days after laser irradiation. Clearly, one single treatment session produced a long-lasting tumor regression.

Example 21. Formulations for Topical Administration

This example shows that Luzitins can diffuse rapidly through the skin when applied with a suitable transdermal formulation. Four minipigs where employed to test the diffusion into the skin of the photosensitizers Luzitin-FMet, and to evaluate the eventual side effects of the formulations for topical administration.

The photosensitizer was first dissolved in absolute ethanol (5 mg in 0.556 ml), next 1.737 ml of propylene glycol were added, followed by 0.22 ml of Azone and 0.3 ml of water. The mixture was thoroughly mixed in vortex and sonicated to facilitate the solubilization, and then added to the gel base, composed of water (76.65%), 96% ethanol (15%) glycerin (6%), triethanolamine (1.35%), carbopol 940 (1%). The mixture is thoroughly mixed to achieve a good homogenization. In this formulation, the final concentration of photosensitizer is 0.1 and that of Azone® in 4%.

The handling of the animals was described above. While calm under the anesthesia, the formulations were applied by hand, using surgical gloves, in pre-determined areas. Each application covered an approximately circular area 3 cm in diameter, with a thickness of a few millimeters of the gel. The application was covered with an occlusive patch. In some animals the same procedure was repeated 3 hour later, in a different area of the back. In one of the animals the formulations were removed 6 h after the application, the back of the animal was cleaned and it was kept alive for 10 days for subsequent evaluation. The skin samples were collected as described before. Each sample was approximately rectangular, with 2 cm sides, and a thickness of 1 cm. None of the animals, and in particular the animal that remained alive, showed evidence for side effects caused by the formulation with our without any of the sensitizers.

After fixative treatment, each sample was cut into slice for evaluations by fluorescence microscopy and by confocal microscopy. A representative example of the images collected from the samples is presented in FIG. 21. The images reveal that, within 3 h of the application of the gel, Luzitin-FMet diffused through all the epidermis. The fluorescence of Luzitin-FMet was further confirmed by its absorption spectrum in FIG. 22. Thus, it is possible to formulate a composition for topical application of Luzitins that diffuses through the stratum corneum and the epidermis within a few hours, which is very convenient for PDT of skin disorders.

(1) K. Berg, in H. Hönigsmann, G. Jori, A. R. Young (Eds.). The Fundamental Bases of Phototherapy. OEMF spa, Milano, 1996, p. 181-207.
(2) R. V. Bensasson, E. J. Land, T. G. Truscott: Excited States and Free Radicals in Biology and Medicine, Oxford Univ. Press, Oxford, 1993.
(3) Y. Vakrat-Haglili, L. Weiner, V. Brumfeld, A. Brandis, Y. Salomon, B. McIlroy, B. C. Wilson, A. Pawlak, M. Rozanowska, T. Sarna, A. Scherz, J. Am. Chem. Soc. 127 (2005) 6487.
(4) M. Pineiro, A. L. Carvalho, M. M. Pereira, A. M. d. A. R. Gonsalves, L. G. Arnaut, S. J. Formosinho, Chem. Eur. J. 4 (1998) 2299.
(5) T. J. Dougherty, D. G. Boyle, K. R. Weishaupt: Photodynamic Therapy—Clinical and Drug Advances, Porphyrin Photosensitization, Plenum Press, New York, 1983.
(6) T. J. Dougherty, C. J. Gomer, B. W. Henderson, G. Jori, D. Kessel, M. Korbelik, J. Moan, Q. Peng, J. Natl. Cancer Inst. 90 (1998) 889.
(7) R. L. Lipson, E. J. Baldes, A. M. Olsen, Natl. Cancer Inst. 26 (1961) 1.
(8) T. J. Dougherty, D. G. Boyle, K. R. Weishaupt, B. Henderson, W. Potter, D. A. Bellnier, K. E. Wityk, Adv. Exp. Biol. Med. 160 (1983) 3.
(9) R. K. Pandey, M. M. Siegel, R. Tsao, J. M. McReynolds, T. J. Dougherty, Biomed. And Environ. Mass Spectrometry 19 (1990) 405.
(10) R. Bonnett, G. Martínez, Tetrahedron 57 (2001) 9513.
(11) E. D. Sternberg, D. Dolphin, C. Brucker, Tetrahedron 54 (1998) 4151.
(12) M. Pineiro, A. M. d. A. Rocha Gonsalves, M. M. Pereira, S. J. Formosinho, L. G. Arnaut, J. Phys. Chem. A 106 (2002) 3787.
(13) Y. Chen, G. Li, R. K. Pandey, Current Org. Chem. 8 (2004) 1105.
(14) E. M. Beems, T. M. A. R. Dubbelman, J. Lugtenburg, J. A. B. Best, M. F. M. A. Smeets, J. P. J. Boehgeim, Photochem. Photobiol. 46 (1987) 639.
(15) S. Schastak, B. Jean, R. Handzel, G. Kostenich, R. Hermann, U. Sack, A. Orenstein, Y. Wang, P. Wiedermann, J. Photochem. Photobiol. B: Biol. 78 (2005) 203.
(16) C. K. Chang, C. Sotiriou, W. Wu, J. Chem. Soc. Chem. Commun. (1986) 1213.
(17) A. R. Morgan, D. Skalkos, G. M. Garbo, R. W. Keck, S. H. Selamn, J. Med. Chem. 34 (1991) 2126.
(18) P. Yong-Hin, T. P. Wijesekera, D. Dolphin, Tetrahedron Lett. 32 (1991) 2875.
(19) G. Zheng, A. Kozyrev, T. J. Dougherty, K. M. Smith, R. K. Pandey, Chemistry Lett. (1996) 119.
(20) A. C. Tome, P. S. S. Lacerda, M. G. P. M. S. Neves, J. A. S. Cavaleiro, Chem Commun (1997) 1199.
(21) H.-J. Kim, J. S. Lindsey, J. Org. Chem. 70 (2005) 5475.
(22) H. W. Whitlock Jr., R. Hanauer, M. Y. Oester, B. K. Bower, J. Am. Chem. Soc. 91 (1969) 7485.
(23) R. Bonnett, R. D. White, U.-J. Winfield, M. C. Berenbaum, Biochem. J. 261 (1989) 277.
(24) F. S. De Rosa. M. V. L. B. Bentley, Pharm. Res. 17 (2000) 1447.
(25) J. L. McCullough, G. D. Weinstein, L. L. Lemus, W. Rampone, J. J. Jenkins, J. Invest. Dermatol. 81 (1983) 528.
(26) O. Santoro, G. Bandieramonte, E. Melloni, R. Marchesini, F. Zunino, P. Lepera, G. De Palo, Cancer Res. 50 (1990) 4501.
(27) J. C. Kennedy, R. H. Pottier, D. C. Pross, J. Photochem. Photobiol. B 6 (1990) 143.
(28) S. R. Wiegell, I.-M. Stender, R. Na, H. C. Wulf, Arch. Dermatol. 139 (2003).
(29) E. G. Azenha, A. C. Serra, M. Pineiro, M. M. Pereira, J. Seixas de Melo, L. G. Arnaut, S. J. Formosinho, A. M. d. A. R. Gonsalves, Chem. Phys 280 (2002) 177.
(30) R. W. Boyle, D. Dolphin, Photochem. Photobiol. 64 (1996) 469.
(31) A. S. M. Ressurreição, M. Pineiro, L. G. Arnaut, A. M. d. A. R. Gonsalves, J. Porphyrins Phthalocyanines 11 (2007) 50.
(32) B. M. Magnusson, W. J. Pugh, M. S. Roberts, Pharm. Res. 21 (2004) 1047.
(33) A. M. d. A. R. Gonsalves, J. M. T. B. Varejão, M. M. Pereira, J. Heterocycl. Chem. 28 (1991) 635.
(34) A. M. D. R. Gonsalves, R. A. W. Johnstone, M. M. Pereira, A. M. P. deSantAna, A. C. Serra, A. J. F. N. Sobral, P. A. Stocks, HETEROCYCLES 43 (1996) 829.
(35) C. J. P. Monteiro, M. M. Pereira, S. M. A. Pinto, A. V. C. Simões, G. F. F. Sá, L. G. Arnaut, S. J. Formosinho, S. Simões. M. F. Wyatt, Tetrahedron 64 (2008) 5132.
(36) C. Serpa, P. J. S. Gomes, L. G. Arnaut, S. J. Formosinho, J. Pina, J. Seixas de Melo, Chem. Eur. J. 12 (2006).
(37) J. M. Dabrowski, M. M. Pereira, L. G. Arnaut, C. J. P. Monteiro, A. F. Peixoto, A. Karocki, K. Urbanska, G. Stochel, Photochem. Photobiol. 83 (2007) 897.
(38) R. Schmidt, C. Tanielian, R. Dunsbach, C. Wolff, J. Photochem. Photobiol. A: Chem. 79 (1994) 11.
(39) M. H. Qvist, U. Hoeck, B. Kreilgaard, F. Madsen, S. Frokjaer, Eur. J. Pharm. Sc. 11 (2000) 59.
(40) J. O'Brien, I. Wilson, T. Orton, F. Pognan, Eur. J. Biochem. 267 (2000) 5421.
(41) M. Niedre, M. S. Patterson, B. C. Wilson, Photochem. Photobiol. 75 (2002) 382-91.
(42) C. Tanielian, C. Schweitzer, R. Mechin, C. Wolff, Free Radic. Biol. Med. 30 (2001) 208-12.
(43) C. Hadjur, N. Lange, J. Rebstein, P. Monnier, H. van der Bergh, G. Wagniéres, J. Photochem. Photobiol. B: Biol. 45 (1998) 170-78.
(44) R. Bonnett, B. D. Djelal, A. Nguyen, J. Porphyrins Phthalocyanines 5 (2001) 652.
(45) R. Bonnett, P. Charlesworth, B. D. Djelal, D. J. McGarvey, T. G. Truscott, J. Chem. Soc., Perkin Trans. 2 (1999) 325.
(46) R. Bonnett, B. D. Djelal, P. A. Hamilton, G. Martinez, F. Wierrani, J. Photochem. Photobiol. B: Biol. 53 (1999) 136-43.

(47) E. Crescenzi, A. Chiaviello, G. Canti, E. Reddi, B. M. Veneziani, G. Palumbo, Mol. Cancer Ther. 5 (2006) 776-85.
(48) D. G. Hilmey, M. Abe, M. I. Nelen, C. E. Stilts, G. A. Baker, S. N. Baker, F. V. Bright, S. R. Davies, S. O. Gollnick, A. R. Oseroff, S. L. Gibson, R. Hilf, M. R. Detty, J. Med. Chem. 45 (2002) 449-61.
(49) A. Hajri, S. Wack, C. Meyer, M. K. Smith, C. Leberquier, M. Kedinger, M. Aprahamian, Photochem. Photobiol. 75 (2002) 140.
(50) H. Rezzoug, L. Bezdetnaya, O. A'amar, J. L. Merlin, F. Guillemin, Lasers Med. Sci. 13 (1998) 119.
(51) C. A. Lipinski, F. Lombardo, B. W. Dominy, P. J. Feeney, Adv. Drug Del. Rev. 46 (2001) 3.

The invention claimed is:

1. A process for the preparation of a chlorin or bacteriochlorin derivative having the formula:

Formula (I)

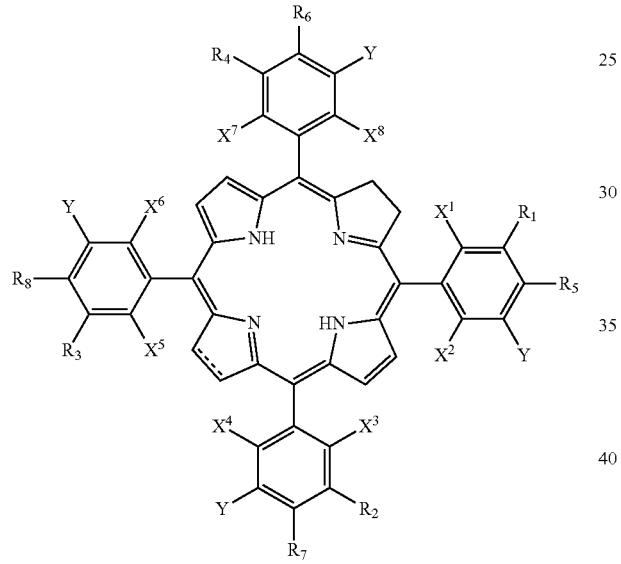

wherein:
- ----- represents a carbon-carbon single bond or a carbon-carbon double bond;
- $X^1$, $X^2$, $X^3$, $X^4$, $X^5$, $X^6$, $X^7$, $X^8$ are each independently chosen from halogen and hydrogen atoms, provided that all members of at least one of (a) the group $X^2$, $X^4$, $X^6$ and $X^8$ and (b) the group of $X^1$, $X^3$, $X^5$ and $X^7$ are halogen atoms, or all of $X^1$, $X^2$, $X^3$, $X^4$, $X^5$, $X^6$, $X^7$, $X^8$ are halogen atoms;
- $R_1$, $R_2$, $R_3$, $R_4$, $R_5$, $R_6$, $R_7$, $R_8$ are each independently chosen from H, —OH and —SO$_2$R, where R is independently chosen from —Cl, —OH, -aminoacid, —OR", —NHR$_n$ and —N(R")$_2$, where R" is alkyl of 1 to 12 carbon atoms;
- Y is one of fluorine or hydrogen;

comprising
(i) the solid state reduction of the corresponding substituted porphyrin to the chlorin derivative or bacteriochlorin derivative using at least one hydrazide in the absence of solvents and in the absence of bases; wherein the corresponding substituted porphyrin has the formula:

Formula (II)

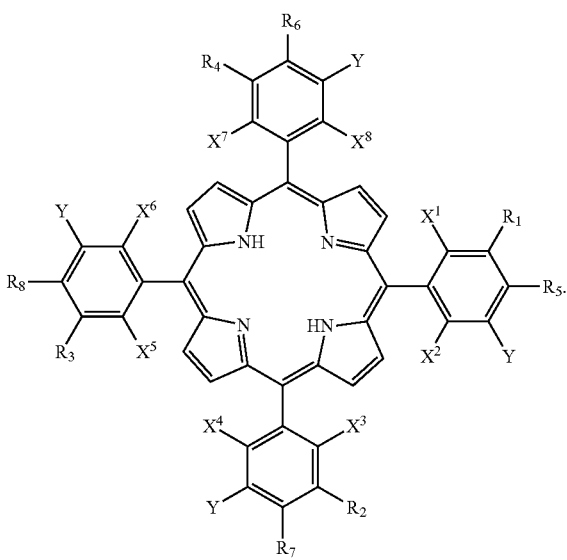

2. A process for the preparation of a chlorin or bacteriochlorin derivative having the formula:

Formula (III)

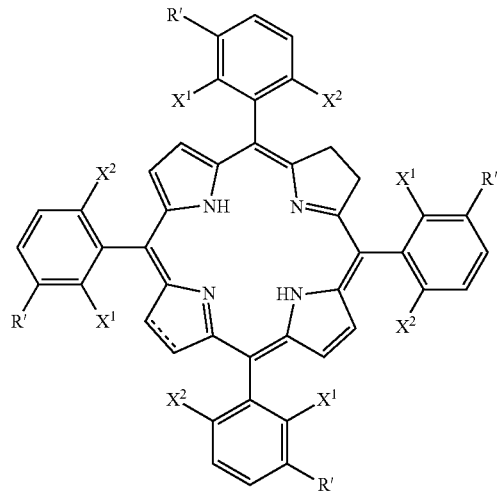

wherein:
- ----- represents a carbon-carbon single bond or a carbon-carbon double bond;
- $X^2$ are independently chosen from halogen, $X^1$ are independently chosen from hydrogen or halogen, and R' are —SO$_2$R;
- where R is independently chosen from —Cl, —OH, -aminoacid, —OR", —NHR" and —N(R")$_2$ where R" is alkyl of 1 to 12 carbon atoms;

comprising
(i) the solid state reduction of the corresponding substituted porphyrin to the chlorin derivative or bacteriochlorin derivative using at least one hydrazide in the absence of solvents and in the absence of bases; wherein the corresponding substituted porphyrin has the formula:

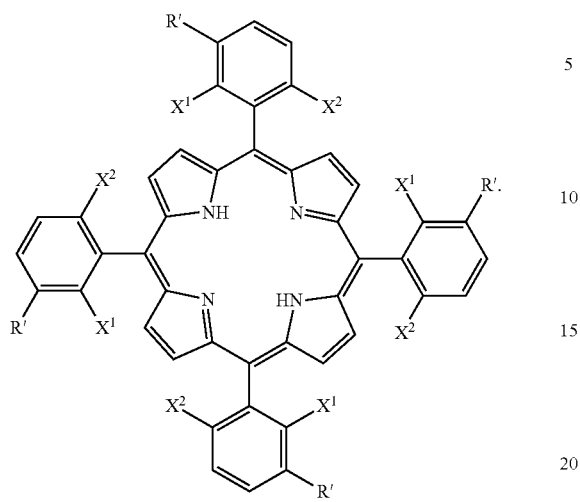

Formula (IV)

3. The process for the preparation of a chlorin or bacteriochlorin derivative according to claim 2, wherein
X² are independently chosen from F, Cl, and Br, and
X¹ are independently chosen from hydrogen or F, Cl, and Br.

4. The process for the preparation of a chlorin or bacteriochlorin derivative according to claim 1, wherein $X^1$, $X^2$, $X^3$, $X^4$, $X^5$, $X^6$, $X^7$, $X^8$ are each independently chosen from F, Cl, Br and hydrogen atoms.

* * * * *